United States Patent
Edwards et al.

(10) Patent No.: US 7,278,425 B2
(45) Date of Patent: Oct. 9, 2007

(54) INHALATION DEVICE AND METHOD

(75) Inventors: David Edwards, Boston, MA (US);
Colleen Conlon, Somerville, MA (US);
David L. Foshee, Apex, NC (US);
Jason R. Durkin, Apex, NC (US); Tim Coker, Merrimack, NH (US); Kevin Stapleton, Boston, MA (US)

(73) Assignee: Alkermes, Inc., Cambridge, MA (US)

( * ) Notice: Subject to any disclaimer, the term of this patent is extended or adjusted under 35 U.S.C. 154(b) by 568 days.

(21) Appl. No.: 10/771,551

(22) Filed: Feb. 5, 2004

(65) Prior Publication Data

US 2004/0154619 A1 Aug. 12, 2004

Related U.S. Application Data

(60) Division of application No. 10/268,059, filed on Oct. 10, 2002, now Pat. No. 6,732,732, which is a continuation-in-part of application No. 09/835,302, filed on Apr. 16, 2001, now Pat. No. 6,766,799.

(51) Int. Cl.
*A61M 15/00* (2006.01)
*A61M 16/00* (2006.01)
*B05D 7/14* (2006.01)
*B65D 83/06* (2006.01)

(52) U.S. Cl. ............................ 128/203.15; 128/203.19; 128/203.21

(58) Field of Classification Search ........... 128/203.15, 128/203.21, 203.19, 203.12; 83/588, 613, 83/636, 684, 620, 633, 691, 622, 467.1, 686; 30/229, 358, 363; 225/13; 606/185
See application file for complete search history.

(56) References Cited

U.S. PATENT DOCUMENTS

| 3,425,414 | A | * | 2/1969 | Roche | 128/203.21 |
| 3,635,219 | A | | 1/1972 | Altounyan et al. | |
| 3,669,113 | A | | 6/1972 | Altounyan et al. | |
| 3,752,027 | A | * | 8/1973 | Gerber et al. | 83/613 |

(Continued)

FOREIGN PATENT DOCUMENTS

CA 2020425 A1 1/1991

(Continued)

OTHER PUBLICATIONS

Bisgaard, H. et al., Fine particle mass from the Diskus inhaler and Turbuhaler inhaler in children with asthma, European Respiratory Journal, 11: 1111-1115 (May 1998).

(Continued)

*Primary Examiner*—Justine R. Yu
*Assistant Examiner*—Kristen Matter
(74) *Attorney, Agent, or Firm*—Covington & Burling LLP; Andrea G. Reister

(57) ABSTRACT

Inhalation device and associated method for facilitating inhalation by a patient of powder medicaments contained in a receptacle. The inhalation device has a chamber for receiving the receptacle. A ring is circumferentially coupled to an inner surface of the chamber to achieve a higher reproducible emitted dose of medicament from the receptacle. The inhalation device also includes an improved implement for puncturing the receptacle, requiring less force and experiencing fewer failures. The inhalation device also includes a means for indicating readiness.

53 Claims, 20 Drawing Sheets

U.S. PATENT DOCUMENTS

| | | | |
|---|---|---|---|
| 3,795,244 A | 3/1974 | Lax et al. | |
| 3,837,341 A | 9/1974 | Bell | |
| 3,888,253 A | 6/1975 | Watt et al. | |
| 3,906,950 A | 9/1975 | Cocozza | |
| 4,013,075 A | 3/1977 | Cocozza | |
| 4,069,819 A | 1/1978 | Valentini et al. | |
| 4,105,027 A | 8/1978 | Lundquist | |
| 4,192,309 A | 3/1980 | Poulsen | |
| 4,240,418 A | 12/1980 | Rosskamp et al. | |
| 4,338,931 A * | 7/1982 | Cavazza | 128/203.15 |
| 4,617,929 A * | 10/1986 | Gill | 606/108 |
| 4,860,740 A | 8/1989 | Kirk et al. | |
| 4,889,114 A | 12/1989 | Kladders | |
| 4,995,385 A * | 2/1991 | Valentini et al. | 128/203.21 |
| 5,152,284 A | 10/1992 | Valentini et al. | |
| 5,239,992 A | 8/1993 | Bougamont et al. | |
| 5,267,965 A * | 12/1993 | Deniega | 604/164.12 |
| 5,301,666 A | 4/1994 | Lerk et al. | |
| 5,314,417 A * | 5/1994 | Stephens et al. | 604/264 |
| 5,349,947 A | 9/1994 | Newhouse et al. | |
| 5,595,175 A | 1/1997 | Malcher et al. | |
| 5,647,349 A | 7/1997 | Ohki et al. | |
| 5,651,359 A | 7/1997 | Bougamont et al. | |
| 5,673,686 A | 10/1997 | Villax et al. | |
| 5,676,683 A * | 10/1997 | Yoon | 606/185 |
| 5,685,294 A | 11/1997 | Gupte et al. | |
| 5,727,546 A | 3/1998 | Clarke et al. | |
| 5,740,794 A | 4/1998 | Smith et al. | |
| 5,785,049 A | 7/1998 | Smith et al. | |
| 5,797,391 A | 8/1998 | Cook et al. | |
| 5,810,004 A | 9/1998 | Ohki et al. | |
| 5,860,419 A | 1/1999 | Davies et al. | |
| 5,896,855 A | 4/1999 | Hobbs et al. | |
| 5,921,236 A * | 7/1999 | Ohki et al. | 128/203.15 |
| 5,921,237 A | 7/1999 | Eisele et al. | |
| 6,089,228 A | 7/2000 | Smith et al. | |
| 6,092,522 A | 7/2000 | Calvert et al. | |
| 6,102,035 A | 8/2000 | Asking et al. | |
| 6,116,237 A | 9/2000 | Schultz et al. | |
| 6,116,238 A | 9/2000 | Jackson et al. | |
| 6,142,145 A | 11/2000 | Dagsland et al. | |
| 6,298,846 B1 * | 10/2001 | Ohki et al. | 128/203.15 |
| 6,367,473 B1 * | 4/2002 | Kafer | 128/203.21 |
| 6,443,152 B1 * | 9/2002 | Lockhart et al. | 128/203.21 |
| 6,543,448 B1 * | 4/2003 | Smith et al. | 128/203.15 |
| 2002/0020067 A1 * | 2/2002 | Silver et al. | 30/226 |
| 2003/0094173 A1 | 5/2003 | Burr et al. | |
| 2005/0056281 A1 * | 3/2005 | Snow | 128/203.21 |

FOREIGN PATENT DOCUMENTS

| | | |
|---|---|---|
| EP | 0 407 276 A2 | 1/1991 |
| EP | 0 506 292 A1 | 9/1992 |
| WO | WO94/08552 A2 | 4/1994 |
| WO | WO 00/64519 A1 | 11/2000 |
| WO | WO 01/07107 | 2/2001 |

OTHER PUBLICATIONS de Boer, A.H. et al., "Inhalation characteristics and their effects on in vitro drug delivery from dry powder inhalers, Part 1. Inhalation characteristics, work on breathing and volunteers' preference in dependence of the inhaler resistance," International Journal of Pharmaceutics 130: 231-244 (1996).

Dunbar, Craig A. et al., A Comparison of Dry Powder Inhaler Dose Delivery Characteristics Using a Power Criterion, PDA Journal of Pharmaceutical Science & Technology, 54(6): 4780484 (Nov./Dec. 2000).

Feddah, Majid R. et al., In-Vitro Characterisation of Metered Dose Inhaler Versus Dry Powder Inhaler Glucocorticoid Products: Influence of Inspiratory Flow Rates, J. Pham. Pharmaceut. Sci. (www.ualberta.ca/-csps) 3(3): 317-324 (2000).

Koskela, T. et al., Efficacy of salbutamol via Easyhaler® unaffected by low inspiratory flow, Respiratory Medicine 94: 1229-1233 (Dec. 2000).

Nielsen, K.G. et al., Flow-dependent effect of formoterol dry-powder inhaled from the Aerolizer®, European Respiratory Journal, 10: 2105-2109 (Sep. 1997).

Richards, Robert and Saunders, Michael, Need for a comparative performance standard for dry powder inhalers, Thorax 48: 1186-1187 (Nov. 1993).

Ross, Danna L. and Schultz, Robert K., Effect of Inhalation Flow Rate on the Dosing Characteristics of Dry Powder Inhaler (DPI) and Metered Dose Inhaler (MDI) Products, Journal of Aerosol Medicine, 9: 215-226 (Nov. 2, 1996).

Smith, Karen J. et al., Influence of Flow Rate on Aerosole Particle Size Distributions from Pressurized and Breath-Actuated Inhalers, Journal of Aerosol Medicine, 11: 231-245 (Nov. 4, 1998).

* cited by examiner

INHALATION DEVICE AND METHOD

CROSS REFERENCE TO RELATED APPLICATIONS

The present application is a divisional of application Ser. No. 10/268,059, filed Oct. 10, 2002, now U.S. Pat. No. 6,732,732, which is a continuation-in-part of application Ser. No. 09/835,302, filed Apr. 16, 2001, now U.S. Pat. No. 6,766,799 the entirety of each of which is incorporated herein by reference.

BACKGROUND OF THE INVENTION

1. Field of the Invention

The present invention relates generally to facilitating release of powder contained in a receptacle. More specifically, the present invention relates to the administration of medication by a method and apparatus for facilitating inhalation of powder medicaments.

2. Related Art

In the medical field, it is often desirable to administer various forms of medication to patients. Well known methods of introducing medication into the human body include the oral ingestion of capsules and tablets, intravenous injection through hypodermic needles, and numerous others. In one method, certain medications may be inhaled into a patient's respiratory tract and lungs through the nose or mouth. Certain of these medications, such as bronchodilators, corticosteroids, etc., for the treatment of asthma and other respiratory anomalies, may be aimed at the respiratory tract directly. Others are inhaled for purposes of systemic treatment, i.e. for treatment of any area of the body through absorption from the respiratory tract through the lung tissue, into the deep lungs, and into the bloodstream. Each of these medications comes in a variety of forms, including fluids, which are commonly administered as an aerosol vapor or mist, as well as solids. Inhalable solids typically take the form of fine, dry powders. Specialized devices, such as inhalers, are provided to assist the patient in directing these fine powder medications into the respiratory tract.

Various types of inhalers are known for the administration of dry powder medicaments. However, each of these inhalers suffers certain drawbacks. For example, U.S. Pat. No. 5,787,881 discloses an inhaler that is used with encapsulated dry powder medicaments. However, use of this device requires numerous steps and imposes a number of inconveniences on a user. For example, the medication capsules used with the device have an aperture formed therein prior to insertion into an opening in the inhaler. Therefore, there exists a danger that an amount of medication may be lost prior to or during insertion into the device. After insertion of the capsule, use of the device requires the additional step that a cover must be closed before the medication may be inhaled.

Inhalation devices configured for use with a capsule containing some type of medicament are shown in U.S. Pat. No. 4,069,819 to Valentini et al. ("the '819 patent") and U.S. Pat. No. 4,995,385 to Valentini et al. ("the '385 patent"). The inhalation device described in the '385 patent was developed to overcome the drawbacks of the device described in the '819 patent. Particularly, in a large number of cases, the device described in the '819 patent experienced irregular and incomplete emptying of the capsule, thereby resulting in difficulties in properly administering the medicament in the capsule. The inhalation device described in the '385 patent attempts to overcome this deficiency by tapering the nebulization chamber toward the end surface that comprises the discharge holes. Thus, the nebulization chamber of the '385 patent is not cylindrical, but rather frusto-conical in form in an attempt to achieve regular complete emptying of the nebulization chamber.

However, further improvements in the design of inhalation devices are needed to achieve high emitted doses and highly dispersed powders while maintaining low resistance, especially when the inhaler is used with high doses and is operated at low peak inspiratory flow rates (PIFR) and low inhalation volumes. As used herein, "emitted dose" (ED) refers to the percentage of the dose of powder medicament that is emitted from a receptacle in the inhalation device. The dispersal of the powder can be quantified by measuring the volume mean geometric diameter (VMGD) of the emitted powder. As used herein "volume mean geometric diameter" refers to the average geometric diameter of the powder. As used herein, "resistance" refers to the square root of the pressure gradient across the inhaler divided by the peak inspiratory flow rate through the inhaler. As used herein "low peak inspiratory flow rate" refers to a peak inspiratory flow rate of approximately 25 L/min or less. Moreover, improvements are needed to achieve high emitted doses and highly dispersed powders that are consistently reproducible, i.e., that have a low standard deviation of emitted dose percentage and VMGD, respectively.

Another drawback of the inhalation devices described in the '819 and the '385 patents is the piercing device that is used to puncture the capsule. Such conventional piercing devices are formed from circular stock, with the points created by pinching the stock at an angle, thereby creating a single sharp cutting edge. Drawbacks of such a design are that the point (which must puncture the capsule material) is often rounded, lessening its effectiveness as a piercing device. Moreover, burrs often form on the lower edge, which can stop the piercing device from retracting from the capsule, thereby causing a device failure. The holes formed by such a conventional piercing device are generally round, and do not have the appearance of being cut by a sharp edge. With such a conventional design, the capsule is often crushed, rather than punctured or pierced. If such a conventional piercing device is used with brittle capsule materials such as gelatin, pieces of capsule material of a size that can be inhaled are usually broken off from the capsule. Thus, conventional piercing devices are less than optimal, particularly for brittle capsule material.

Another drawback of conventional inhalation devices is that they have no means for indicating when the powder in the inhaler is ready for inhalation by the user. It is desirable to have a means for indicating to the user that a dose of powder is ready for inhalation. For example, it would be desirable for a patient using a device for dispensing fluticasone propionate (used to treat asthma) to know when the device is ready for inhalation.

Thus, there is a need in the art for an improved method and apparatus for inhalation of dry powder medicaments. What is needed is an inhaler that provides for a higher emitted dose that is consistently reproducible with low standard deviation. Such a need is particularly acute for low peak inspiratory flow rates, and for high dosage ranges. There is a further need in the art for an improved means for puncturing the capsule containing the medicament. The present invention, the description of which is fully set forth below, solves the need in the art for such improved methods and apparatus.

SUMMARY OF THE INVENTION

The present invention relates to a method and apparatus for facilitating release of powder from a device. In one aspect of the invention, a device for emitting powder is provided. The device includes a first casing portion, and a second casing portion removably coupled to the first casing portion. A cylindrical chamber, defined by a straight wall of circular cross section, is coupled to the first casing portion. The chamber has a proximal end and a distal end. A ring is circumferentially coupled to an inner surface of the chamber. The ring is preferably disposed at approximately a midpoint of the chamber, or, alternatively, disposed adjacent the proximal end of the chamber. The second casing portion includes an emitter portion disposed at the proximal end of the chamber when the first and second casing portions are coupled together. The emitter portion defines at least one aperture configured to emit powder therethrough.

In another aspect of the present invention, the device is configured as an inhalation device for administering powder. In this aspect of the present invention, the emitter portion is configured as an inhalation portion so that powder is dispersed in the chamber and administered to a user through the inhalation portion. The inhalation portion may be configured as a mouth piece for inhalation through the mouth, or as a nose piece for inhalation through the nose.

One aspect of the invention comprises an optimized configuration of a device for administering powder that comprises a chamber defined by a wall and configured to hold a receptacle containing a powder, the wall defining a plurality of vents, and the inhalation device further comprising an inhalation portion defining at least one aperture for emitting powder therethrough. The inhalation device is configured to have a resistance of at most 0.28 (cm $H_2O)^{1/2}$/L/min and to provide an emitted dose of at least 85% when the dose of powder is up to 20 mg and when the device is operated at a peak inspiratory flow rate of 25 L/min or less and at an inhalation volume of 0.75 L or less. Preferably the standard deviation of the emitted dose is 10% or less.

In another aspect, the device of the present invention is configured to cause the emitted powder to be highly dispersed. By "highly dispersed" is meant that the VMGD of the emitted powder is substantially similar to the VMGD of the powder contained in the receptacle. Highly dispersible powders have a low tendency to agglomerate, aggregate or clump together and/or, if agglomerated, aggregated or clumped together, are easily dispersed or de-agglomerated as they emit from an inhaler and are breathed in by the subject. Typically, the highly dispersible particles suitable in the methods of the invention display very low aggregation compared to standard micronized powders which have similar aerodynamic diameters and which are suitable for delivery to the pulmonary system. Properties that enhance dispersibility include, for example, particle charge, surface roughness, surface chemistry, relatively large geometric diameters, and the configuration of the device used to dispense the powder.

In another aspect of the invention, the powder is contained in a receptacle that is disposed in the chamber. Upon puncturing the receptacle, powder is dispersed in the chamber and emitted or inhaled from the device.

In yet another aspect of the present invention, the device of the present invention includes means for puncturing the receptacle. In one embodiment, the means for puncturing can be configured as a staple. Such a staple is preferably configured in a substantially U-shape, having two prongs. In one aspect of the present invention, each of the prongs has a square cross-section. In another aspect of the present invention, the substantially U-shaped staple includes a rounded portion and two prongs that define a non-planar inner edge and a non-planar outer edge of the staple, the staple being formed from a rectangular length having two end surfaces and four planar side surfaces that intersect to form four non-planar edges. The inner edge of the staple is configured to be one of the non-planar edges, and the outer edge of the staple is the non-planar edge that is opposite that non-planar edge. Each end surface is an angled diamond-shaped surface. In a preferred aspect, each end surface has a top point at an apex of the inner edge, and a bottom point at an apex of the outer edge, each top point forming a cutting point for one of the prongs.

In another embodiment, the puncturing means can be configured as a substantially longitudinal prong comprising a puncturing surface on the distal end of the prong, a primary cutting surface running from the proximal end to the distal end of the prong and terminating at the puncturing surface, and a substantially planar face opposite to the primary cutting edge and running from the proximal end to the distal end of the prong. Another embodiment of the puncturing means comprises a substantially longitudinal prong comprising a puncturing surface on the distal end, a primary cutting surface terminating at the puncturing surface, and a face opposite to the primary cutting edge, wherein the prong is configured to create an opening in a wall by forming a hanging chad in the wall, the hanging chad having a free end formed by the puncturing surface and the primary cutting edge and a hinge coupled to the wall formed by the face. In another embodiment, the prong is configured to form a hanging chad in a wall of the receptacle having a longitudinal axis substantially parallel to the prong and a minor axis substantially perpendicular to the longitudinal axis, the hanging chad being opened to an angle of at least 30 to 45 degrees with respect to the minor axis of the receptacle. In another embodiment the prong is configured so that at least ¾ of the length of the prong can be inserted into a receptacle without breaking off chads in the receptacle.

In each of these embodiments, the prong preferably has an angled surface at the distal end, the surface having a distal end terminating at the puncturing surface and a proximal end terminating at the substantially planar face. In addition, the prong preferably is tapered, so that its distal end is smaller than its proximal end, to facilitate removing the prong from the receptacle. The prong also preferably has a plurality of longitudinal faces and a plurality of longitudinal edges running from the proximal end to the distal end of the prong. In one embodiment, the cross section of the prong is a pentagon. In a related embodiment, the width of the substantially planar face may be very small and the four longitudinal faces may be substantially at right angles to each other so that the prong has substantially a diamond shaped cross section. In another embodiment, the cross section of the prong is a triangle.

In another embodiment of the invention, the puncturing means comprises one or more of the longitudinal prongs coupled to a base, preferably in a U-shape. In another aspect of the invention, any of these embodiments of the longitudinal prongs may be coupled to the device for administering powder.

In still a further aspect of the present invention, a method for dispensing powder by inhalation is provided. Such a method comprises providing a powder inhalation device, the device comprising
   a first casing portion, a cylindrical chamber, defined by a straight wall of circular cross-section, coupled to said first casing portion, said chamber having a proximal end and a distal end and configured to receive a receptacle therein, said chamber comprising a ring circumferentially coupled to an inner surface of said chamber, and a second casing portion removably coupled to said first casing portion, said second casing portion comprising an inhalation portion disposed at the proximal end of said chamber when said first and said second casing portions are coupled, said inhalation portion comprising a hemispheric region defining a plurality of apertures configured to emit powder therethrough;

puncturing the receptacle to allow release of powder into said chamber; and dispersing powder through inhalation of the powder through said inhalation portion.

In one aspect of the present invention, the inhaling step is carried out by inhaling the powder through a mouthpiece into a user's mouth. Alternatively, the inhaling step may be carried out by inhaling the powder through a nose piece into a user's nose.

The present invention also encompasses an indicating device comprising a body disposed within a casing and reversibly moveable between a first and a second position, an indicator moveable between a rest position and an indicating position, and a means for coupling the body and the indicator, wherein upon a first movement of the body from the first position to the second position, the means for coupling couples the body and the indicator, and upon a second movement of the body from the second position to the first position, the indicator moves from the rest position to the indicating position.

In another embodiment, the present invention encompasses an indicating device comprising a body disposed within a casing and reversibly moveable between a first position and a second position, an indicator reversibly moveable between a rest position and an indicating position, a lip coupled to the indicator and a flange coupled to the body for engaging the lip, wherein upon a first movement of the body from the first position to the second position, the flange engages the lip, and upon a second movement of the body from the second position to the first position, the engagement of the lip and the flange causes the indicator to move from the rest position to the indicating position.

The invention further encompasses one of the previously described embodiments of a device for emitting powder comprising a means for indicating readiness of the device for emitting powder. The means for indicating readiness of the device for emitting powder may comprise one of the previously described embodiments of an indicating device.

In addition, the invention comprises a method for indicating the readiness of a device for emitting a medicament. Such a method comprises providing a device for dispensing a medicament, the device comprising a casing comprising at least one aperture configured to emit powder therethrough, a body coupled to said casing and reversibly moveable between a first position and a second position, and an indicator coupled to said casing and reversibly moveable between a rest position and an indicating position;

applying an axial force to said body to move said body from said first position to said second position, which readies the powder for dispensing and couples said body to said indicator;

releasing said axial force from said body to allow said body to move from said second position to said first position, which moves said indicator to said indicating position; and dispensing the medicament from said device.

The invention further comprises a method for indicating that a device for dispensing a medicament has been used. Such a method comprises providing a device for dispensing a medicament, the device comprising a casing comprising at least one aperture configured to emit a medicament therethrough, a body coupled to said casing and reversibly moveable between a first position and a second position, and an indicator coupled to said casing and reversibly moveable between a rest position and an indicating position;

applying an axial force to said body to move said body from said first position to said second position, which couples said body to said indicator;

dispensing the medicament from the device;

releasing said axial force from said body to allow said body to move from said second position to said first position, which moves said indicator to said indicating position to indicate that the device has been used.

Features and Advantages

One feature of the present invention is that it provides, in a low resistance inhaler with a highly dispersed powder, high emitted doses that are consistently reproducible over a range of peak inspiratory flow rates, inhalation volumes and dosage quantities. Advantageously, the present invention improves and optimizes the emitted dose at low peak inspiratory flow rates, low inhalation volumes, and high dose ranges. A particularly advantageous feature of the present invention is its ability to operate at low peak inspiratory flow rates, such as would be associated with a child, an elderly person, or a person with a respiratory disease, such as chronic obstructive pulmonary disease (COPD).

One advantage of the present invention is that the means for puncturing used in the device is less expensive to manufacture than conventional piercing devices. Advantages of the injection molding manufacturing process used for the puncturing means include reliability, reproducibility, and design flexibility, such as the ability to make a wide variety of shapes and sizes of longitudinal prongs. For example, larger longitudinal prongs of the present invention can create larger openings in the receptacles than conventional piercing devices, which allows for higher emitted doses at low peak inspiratory flow rates, low volumes, and high dosage quantities. Another advantage of the present invention is that at least one configuration of the puncturing means facilitates forming a hanging chad in the wall of the receptacle, with an opening of at least 30 to 45 degrees, to facilitate more efficient removal of powder from the receptacle and, thus, higher emitted doses than could be achieved with conventional piercing devices. Moreover, the means for puncturing of the present invention advantageously provides improved puncturing performance since less force is needed to puncture the receptacles, and fewer failures result than with conventional piercing devices. Yet another advantage is that the prongs are shaped for easy removal from the receptacle without breaking off the hanging chad formed in the wall of the receptacle.

Another advantage of the preferred means for puncturing is an improvement to the emitted dose rate of the inhaler. In one aspect of the invention, the puncturing means improves the powder flow from the receptacle by increasing the size of the holes in the receptacle. In another aspect of the invention, the puncturing means improves the peak inspiratory flow rate by opening a hanging chad in the wall of the receptacle to an angle of at least 30 to 45 degrees with respect to the wall of the receptacle. Consequently, the emitted dose of the powdered medicament delivered to a patient will be independent of how fast the patient breathes, thereby ensuring that a consistent dose of medicament is delivered each time. Another advantageous feature of the present invention is the accuracy of medicament dosage delivered thereby. Since only one dosage of medication is present in the inhaler during each use, the possibility of overdose is eliminated, and the medicament need not be metered prior to delivery. A patient may simply inhale all medicament present in the device. Yet another advantage is the design of the puncturing means allows for a greater range of puncturing depths without breaking off the chads formed in the receptacle, allowing for greater optimization of the inhaler.

Because the present invention operates only under the inhalative power of the patient, the inhaler carries the additional advantage that no accessory device, such as a compressed air cylinder or other propellant, needs to be used in conjunction with the present invention.

Another advantage of the present invention is that during inhalation, the medicament is subjected to mixing in the dispersion chamber. This helps to ensure that the medicament exiting the inhaler and entering the patient's respiratory system is in the form of a fine dry powder, facilitating medicament deposition in the lungs. In addition, inhalation of finer powders is typically more comfortable for the patient.

Still another advantage of the present invention is that it can be used with individuals who cannot breathe hard, such as a child, an elderly person, or a person suffering from a respiratory disease, such as asthma, or individuals who are sleeping or in a coma.

Yet another advantage of the apparatus of the present invention is that it is reusable. To reuse, a patient removes the emptied receptacle, and replaces it with a fresh receptacle filled with the proper dose of medicament.

Another advantage of the present invention is that it includes a means for indicating when a device for emitting powder is ready for inhalation. Such a means for indicating informs the user when the device is ready for use and/or when the device needs to be refilled or discarded. For example, the means for indicating could be used with a device for emitting fluticasone propionate (used to treat asthma) to indicate that the device is ready for inhalation. Alternatively, the means for indicating could be used with an epinephrine pen for treating allergies to indicate that the pen has been used. In addition, the means for indicating preferably makes an audible click so that a user will know when the device has been properly actuated. Also, the means for indicating is easy to manufacture and use.

BRIEF DESCRIPTION OF THE FIGURES

The present invention is described with reference to the accompanying drawings. In the drawings, like reference numbers indicate identical or functionally similar elements.

DETAILED DESCRIPTION OF THE PREFERRED EMBODIMENTS

Overview

Figure 1:
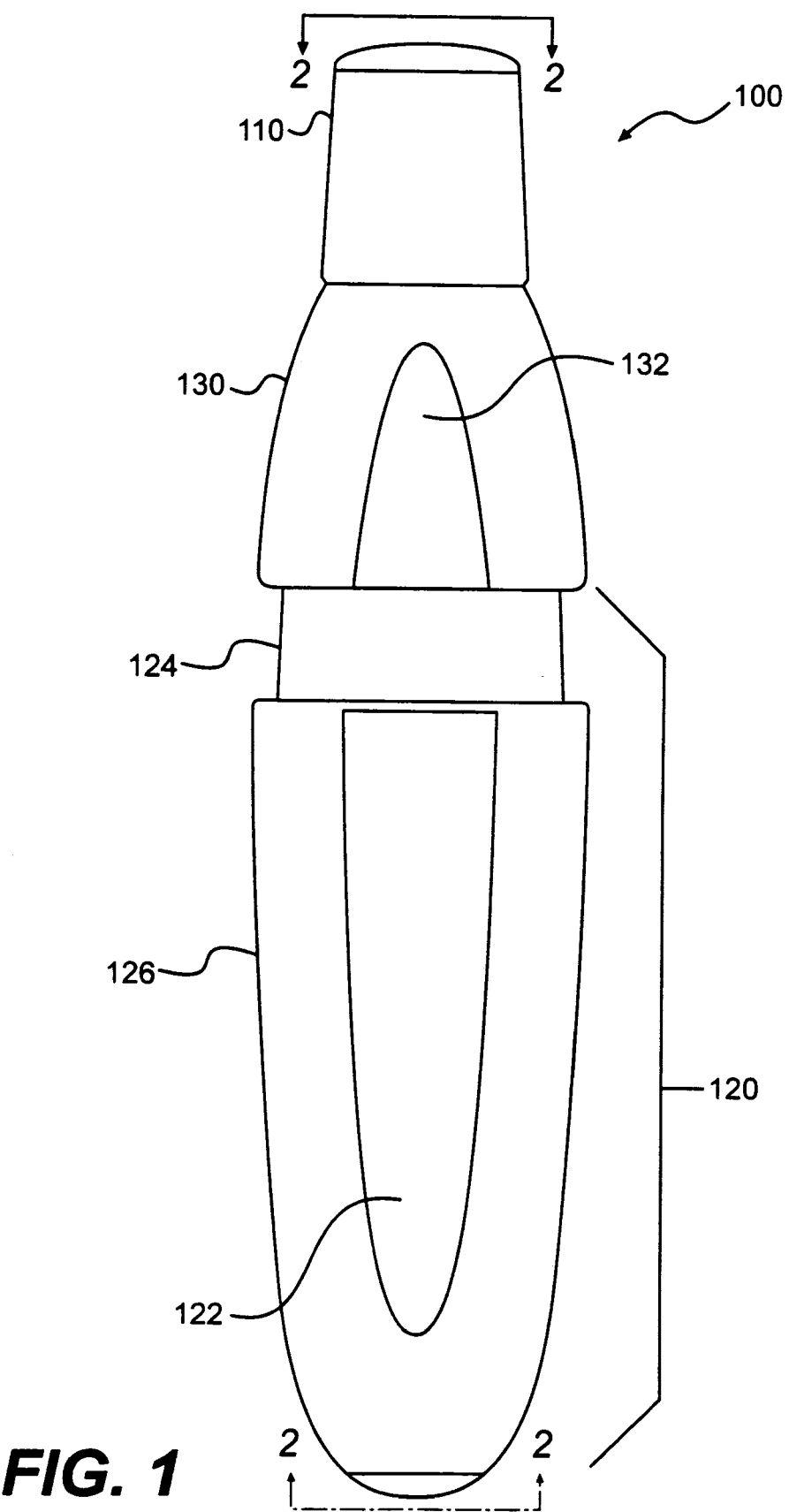
FIG. 1 is a front view of one embodiment of a device of the present invention.

The present invention provides an improved method and apparatus for facilitating release of powder. In a preferred embodiment, the powder is contained in a receptacle. As used herein, the term "receptacle" includes but is not limited to, for example, a capsule, blister, film covered container well, chamber, and other suitable means of storing a powder known to those skilled in the art. The present invention will be described below in the context of a method and apparatus for dispensing dry powder medicaments for inhalation by a patient. However, it should be apparent to one skilled in the art that the invention is not limited to such an exemplary embodiment, and could be used for other purposes.

As will be described in more detail below, an apparatus of the present invention is an inhaler that includes a chamber. In one embodiment, the chamber is configured to receive the receptacle containing the medicament. To improve the emptying of the receptacle and provide a higher reproducible emitted dose, the chamber includes a ring circumferentially coupled to an inner surface of the chamber. The ring is preferably disposed at approximately a midpoint of the chamber, or alternatively, adjacent the proximal end of the chamber. In proper use, air will exit the inhaler carrying a full dose of medicament in the form of a fine, dry powder.

Another aspect of the present invention is an optimized chamber configured to have a resistance of at most 0.28 (cm $H_2O)^{1/2}$/L/min and to provide an emitted dose of at least 85% when the dose of powder is up to 20 mg and when the device is operated at a peak inspiratory flow rate of 25 L/min or less and at an inhalation volume of 0.75 L or less.

The inhaler of the present invention is preferably configured with a means for puncturing the receptacle that improves puncturing performance, particularly with brittle receptacle material. In one preferred embodiment, the means for puncturing the receptacle of the present invention is configured as a substantially U-shaped staple with two prongs, each prong having a sharp point and two cutting edges. In one such embodiment, each prong has a square cross-section, with the staple material being bent around a face so that the innermost part of the U-shaped staple is flat. In another such embodiment, the staple material is rotated 45 degrees so that it is bent around an edge so that the innermost part of the U-shaped staple is an edge. In such an embodiment, the end surface of each prong is an angled diamond-shaped surface.

In another preferred embodiment, the means for puncturing the receptacle is configured as a substantially longitudinal prong comprising a puncturing surface on the distal end, a primary cutting surface running from the proximal end to the distal end of the prong and terminating at the puncturing surface, and a substantially planar face opposite to the primary cutting edge and running from the proximal end to the distal end of the prong. The prong preferably has an angled surface at the distal end, the angled surface having a distal end terminating at the puncturing surface and a proximal end terminating at the substantially planar face. In addition, the prong is preferably tapered so that the distal end is smaller than the proximal end, to facilitate removing the prong from a receptacle. The prong also preferably has a plurality of longitudinal faces and a plurality of longitudinal edges running from the proximal end to the distal end of the prong.

The prong is configured to create an opening in a wall by forming a hanging chad in the wall, the hanging chad having a free end formed by the puncturing surface and the primary cutting edge and a hinge coupled to the wall formed by the face. In a preferred embodiment, the prong is configured to open the hanging chad to an angle of at least 30 to 45 degrees between the minor axis of the receptacle and the hanging chad, wherein the minor axis is substantially perpendicular to a longitudinal axis of the receptacle, which is substantially parallel to the longitudinal prong.

The methods of the present invention use an inhaler to dispense powder by inhalation. As will be discussed in greater detail below, a user operates the device to puncture the receptacle to disperse powder in the chamber, and inhales the powder through the inhalation portion. The present invention further encompasses a means for indicating readiness coupled to a device for administering powder.

Inhaler and Associated Method of the Present Invention

A front view of one embodiment of an inhalation device 100 of the present invention is shown in FIG. 1. The rear view of device 100 is substantially identical to the front view. Device 100 includes a first or lower casing portion 120 and a second or upper casing portion 130 removably coupled to first casing portion 120. Upper casing portion 130 and lower casing portion 120 include a flattened region 132 and 122, respectively, for ease of gripping the casing for use by a patient. Lower casing portion 120 preferably includes an outer casing 126 and an inner casing 124 movably received within outer casing 126. A removable cap 110 is provided at the user or inhalation end of the device.

Preferred materials for device 100 include Food and Drug Administration (FDA) approved, USP tested plastics. Preferably, device 100 is manufactured using an injection molding process, the details of which would be readily apparent to one skilled in the art.

FIG. 2 is a cross-section of device 100 shown in FIG. 1 along line 2-2. As shown in FIG. 2, device 100 includes an inhalation or emitter portion 220. Inhalation portion 220 comprises a hemispheric region 222 that defines a plurality of apertures 224. It should be understood that the present invention is not limited to a particular number of apertures 224, and can be configured such that at least one aperture 224 is provided. An inhalation piece 226 is provided to allow for inhalation of the medicament by a user. Inhalation piece 226 can be configured as a mouth piece for inhalation through a user's mouth. Alternatively, inhalation piece 226 can be configured as a nose piece for inhalation through a user's nose.

Device 100 includes a cylindrical chamber 210 that is defined by a straight wall 212 of circular cross-section. Chamber 210 has a proximal end 214 and a distal end 216. A plurality of vents 218 are defined by wall 212, and are configured for introducing air into chamber 210 to disperse powder released from a capsule 219. It should be understood that the present invention is not limited to a particular number of vents 218, and can be configured such that at least one vent 218 is provided. Powder released from capsule 219 is dispersed in chamber 210 and inhaled through apertures 224 and inhalation piece 226 by the user.

In other embodiments of the invention, receptacles other than capsules are used, such as blisters and film covered container wells as is known in the art. In one embodiment, the volume of the receptacle is at least about 0.37 $cm^3$. In another embodiment, the volume of the receptacle is at least about 0.48 $cm^3$. In yet another embodiment, the receptacles have a volume of at least about 0.67 $cm^3$ or 0.95 $cm^3$. In one embodiment of the invention, the receptacle is a capsule designated with a capsule size 2, 1, 0, 00, or 000. Suitable capsules can be obtained, for example, from Shionogi (Rockville, Md.). Blisters can be obtained, for example, from Hueck Foils, (Wall, N.J.).

The receptacle encloses or stores particles, also referred to herein as powders. The receptacle is filled with particles in a manner known to one skilled in the art. For example, vacuum filling or tamping technologies may be used. Generally, filling the receptacle with powder can be carried out by methods known in the art. In one embodiment of the invention, the particle or powder enclosed or stored in the receptacle have a mass of at least about 5 milligrams (mg). In another embodiment, the mass of the particles stored or enclosed in the receptacle is at least about 10 mg, and up to approximately 50 mg. In a preferred embodiment, the mass of the particles is approximately 20 mg.

In one embodiment of the present invention, particles used with the device have a tap density of less than about 0.4 g/cm$^3$. Particles having a tap density of less than about 0.4 g/cm$^3$ are referred to herein as "aerodynamically light". In a preferred embodiment, the particles have a tap density of near to or less than about 0.1 g/cm$^3$. Tap density is a measure of the envelope mass density characterizing a particle. The envelope mass density of particles of a statistically isotropic shape is defined as the mass of the particle divided by the minimum sphere envelope volume within which it can be enclosed. Features that can contribute to low tap density include irregular surface texture and hollow or porous structure. Particularly preferred particles and powders are described in U.S. Pat. Nos. 6,136,295, 5,985,309, 5,874,064, and 5,855,913, and U.S. patent application Ser. No. 09/591,307, filed Jun. 9, 2000 entitled "High Efficient Delivery of a Large Therapeutic Mass Aerosol", the entirety of each of the foregoing patents and patent applications is hereby incorporated herein by reference.

Device 100 includes a means for puncturing 230 that is used to puncture capsule 219 to release powder contained therein into chamber 210. In the embodiment shown in FIG. 1, means for puncturing 230 is configured as a substantially U-shaped staple having two prongs 232. In this embodiment, each of prongs 232 is configured with a square cross-section 234, thereby providing a sharp point and two cutting edges. This will be discussed in more detail below with respect to FIGS. 9A and 9B. As discussed in more detail below, device 100 could alternatively be configured with the means for puncturing shown in FIGS. 7A through 7D. Also, device 100 could alternatively be configured with the means for puncturing shown in FIGS. 16A through 16D. As can be readily appreciated by one skilled in the art, the present invention is not limited to these means for puncturing the capsule, described in detail below. For example, one, or a plurality of, straight needle-like implements could be used. Preferably, the means for puncturing is configured to puncture at least two holes in the capsule.

Means for puncturing 230 is preferably configured to be movable between a non-puncturing position (as depicted in FIG. 1) and a puncturing position. In the puncturing position, prongs 232 pierce or puncture capsule 219 to make holes therein. In a preferred embodiment, a means for biasing is provided that biases the means for puncturing 230 in the non-puncturing position. In the embodiment shown in FIG. 2, the means for biasing is configured as a spring 242 that biases the substantially U-shaped staple in the non-puncturing position.

Figure 2:
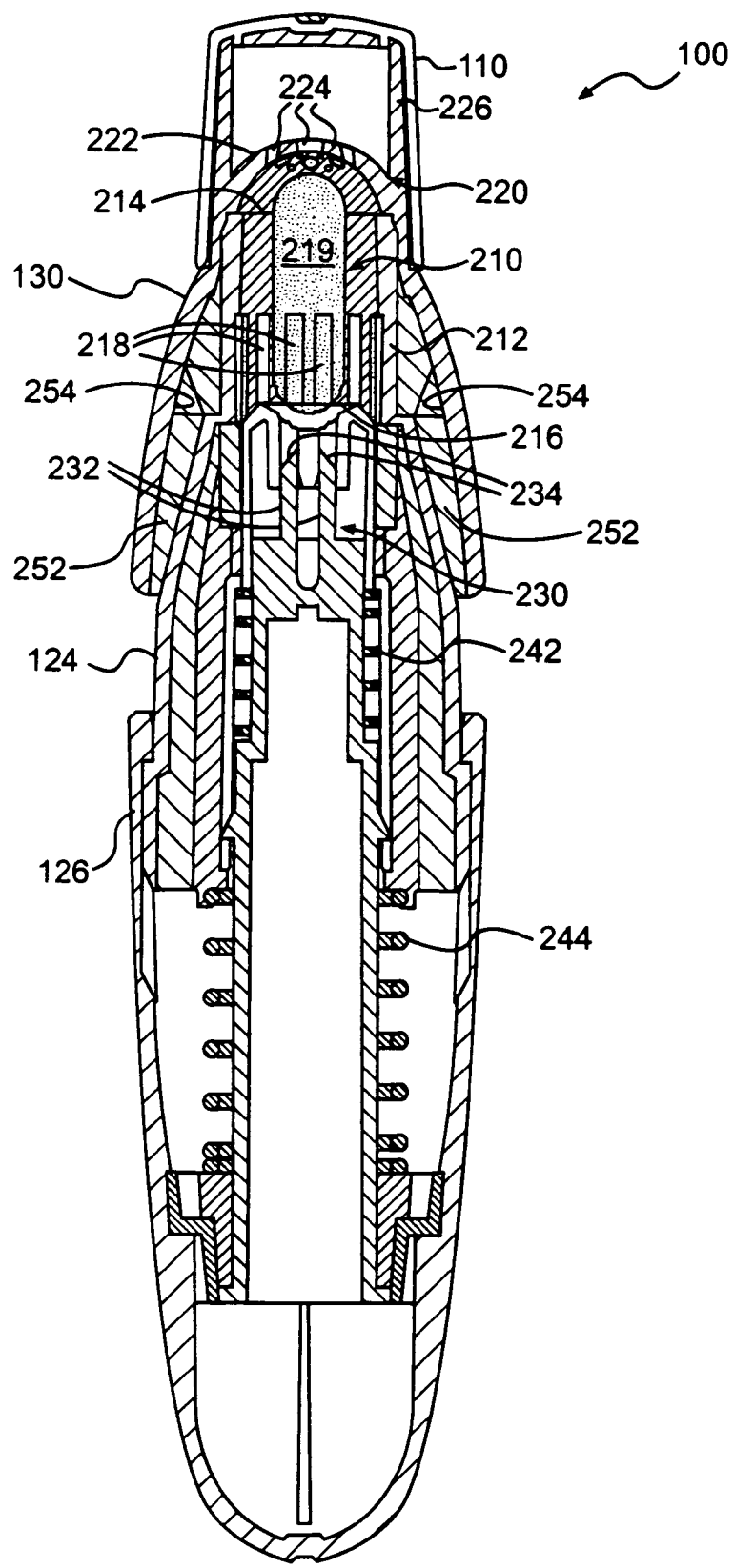
FIG. 2 is a cross-section of the device shown in FIG. 1 along line 2-2.

As noted with respect to FIG. 1, device 100 includes inner casing 124 and outer casing 126. As shown in FIG. 2, a spring 244 is disposed in lower casing portion 120 that biases inner casing 124 in an outward position. Upon compression of spring 244, inner casing 124 moves from the outward position to an inward position, thereby drawing lower casing portion 120 toward upper casing portion 130. Compression of spring 244 also causes compression of spring 242, thereby causing means for puncturing 230 to move to the puncturing position. Upon release of compression, springs 242 and 244 return to their biased state, thereby returning means for puncturing 230 to its non-puncturing position, and inner casing 124 to its outward position.

A pair of flanges 252 is disposed on first casing portion 120. A pair of grooves 254 is disposed on second casing portion 130 so that flanges 252 can be received within grooves 254 to thereby couple the first and second casing portions. Preferably, the first and second casing portions are coupled with a friction-fit engagement. A friction-fit engagement can be achieved using the groove and flange arrangement depicted in FIG. 2. Other alternative configurations for a friction-fit engagement would be readily apparent to one skilled in the art.

Figure 3:
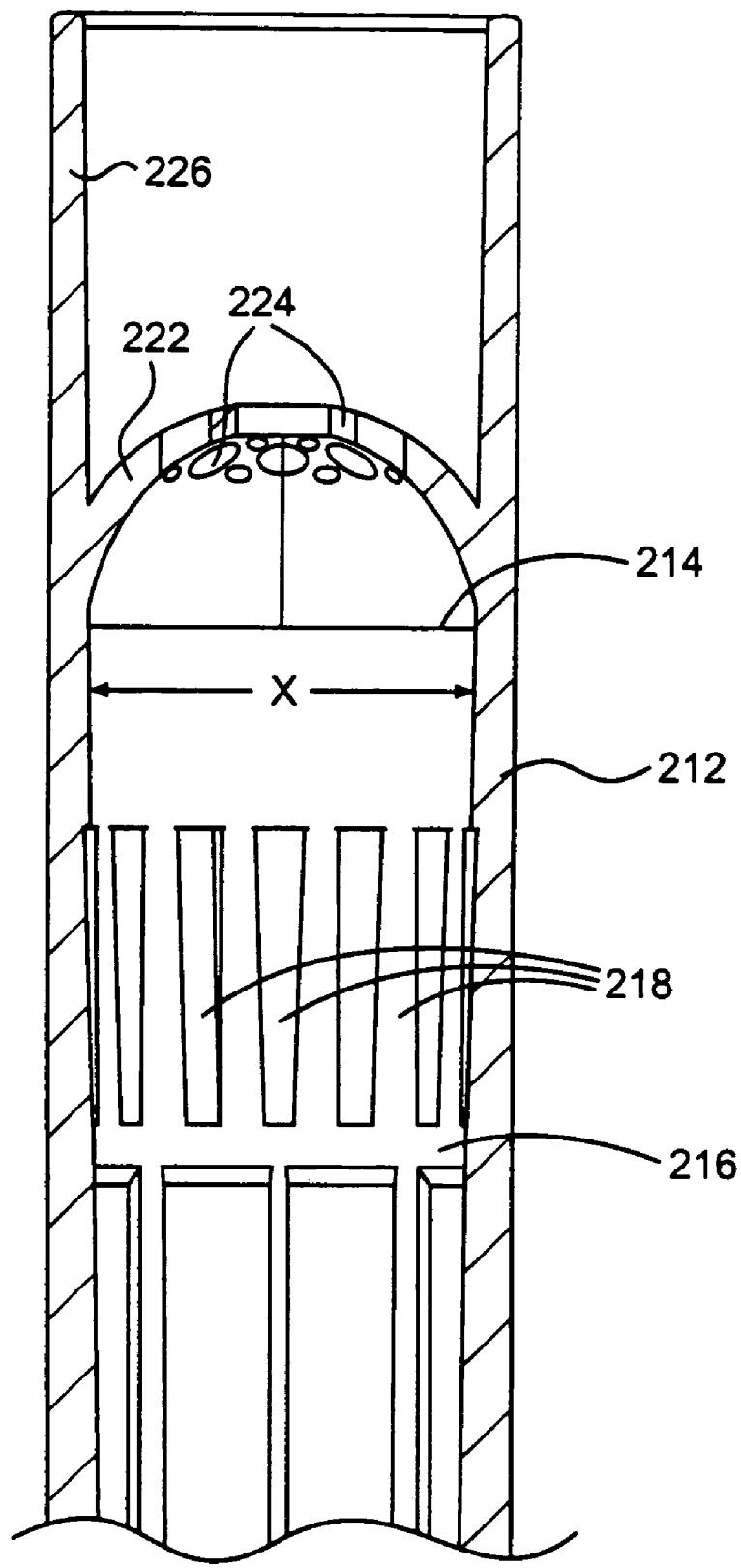
FIG. 3 is an enlarged partial cross-section of one embodiment of a dispersion chamber of the present invention.

FIG. 3 is an enlarged partial cross-section of one embodiment of chamber 210. In the embodiment shown in FIG. 3, chamber 210 does not contain a ring disposed on an inner surface, and an inner diameter of chamber 210 is depicted as "X". Such a configuration may be referred to herein as a "straight" chamber configuration.

Figure 4:
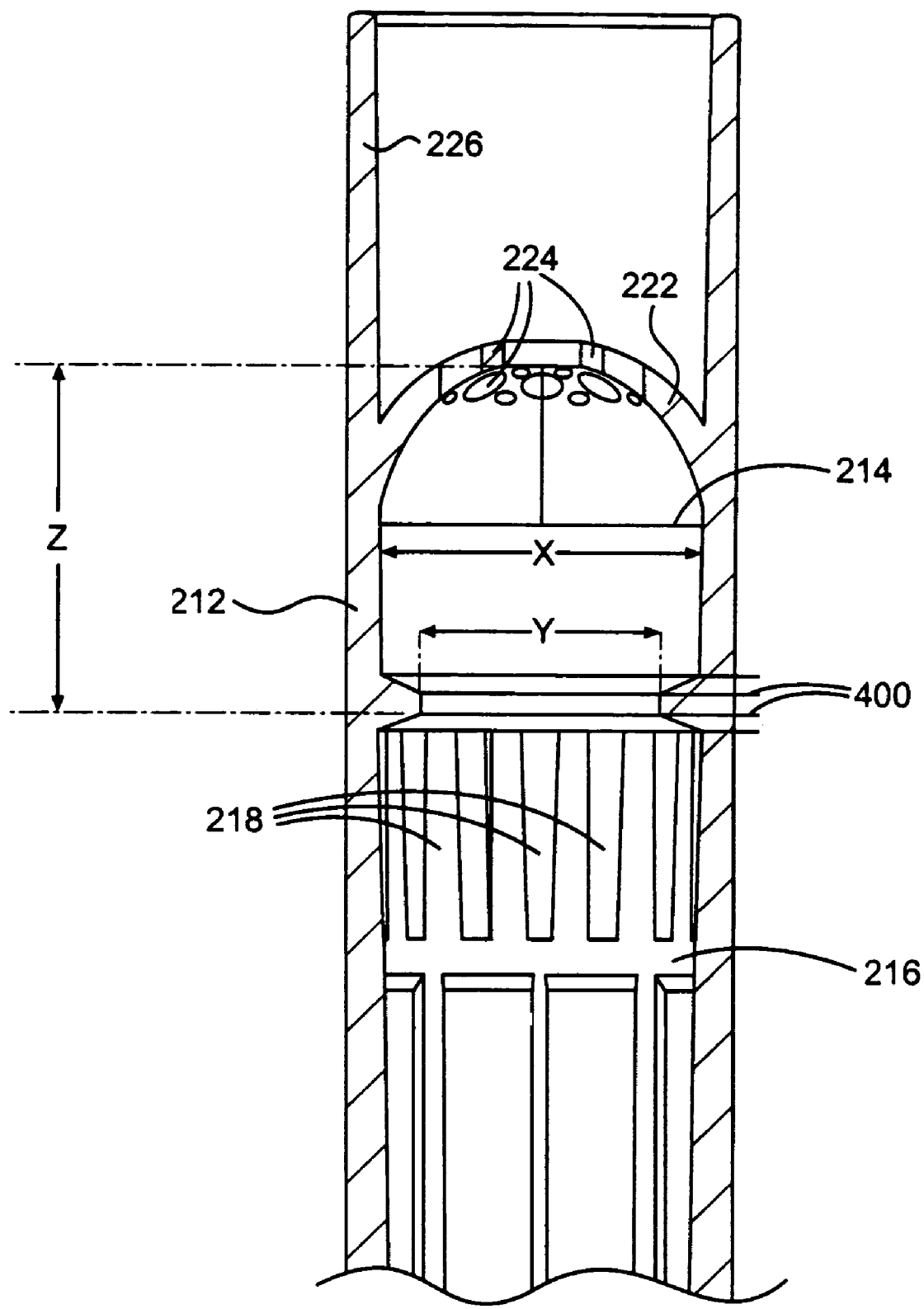
FIG. 4 is an enlarged partial cross-section of another embodiment of a dispersion chamber of the present invention showing one location for a ring in the dispersion chamber.

FIG. 4 is an enlarged partial cross-section of another embodiment of chamber 210. In the embodiment shown in FIG. 4, a ring 400 is circumferentially coupled to an inner surface of chamber 210. An inner diameter of ring 400 is depicted as "Y", and is less than inner diameter X of chamber 210. In the embodiment shown in FIG. 4, ring 400 is disposed at approximately a midpoint of chamber 210. Such a configuration may be referred to herein as a "low" ring position or "low" chamber configuration. As shown in FIG. 4, in the low ring position, ring 400 is disposed adjacent vents 218. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 4, diameter X is 0.47 in., diameter Y is 0.38 in., and distance Z is 0.49 in.

Figure 6:
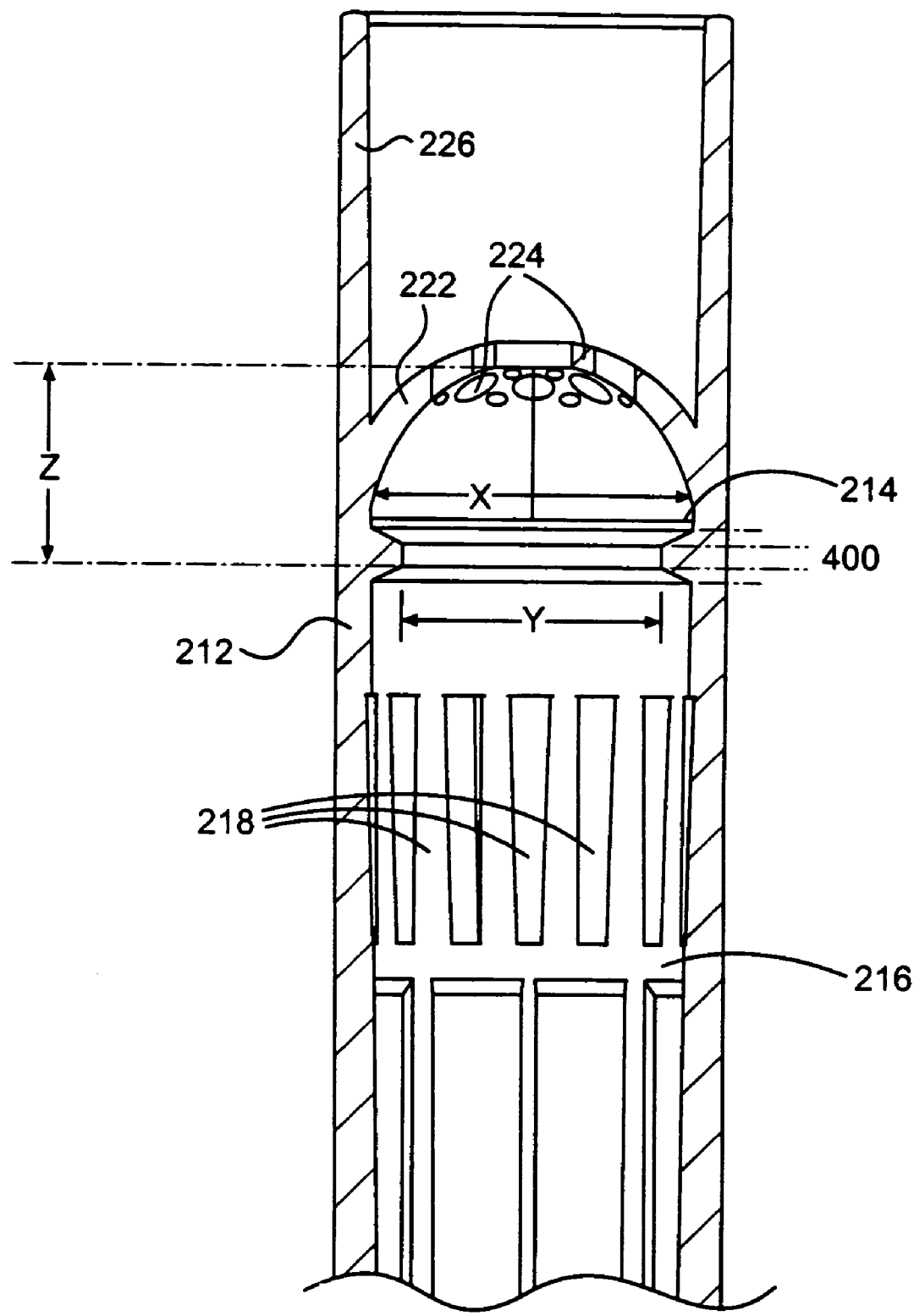
FIG. 6 is an enlarged partial cross-section of another embodiment of a dispersion chamber of the present invention showing another location for a ring in the dispersion chamber.

FIG. 6 is an enlarged partial cross-section of another embodiment of chamber 210. In the embodiment shown in FIG. 6, ring 400 is circumferentially coupled to an inner surface of chamber 210. An inner diameter of ring 400 is depicted as "Y", and is less than inner diameter X of chamber 210. In the embodiment shown in FIG. 6, ring 400 is disposed adjacent the proximal end of chamber 210. Such a configuration may be referred to herein as a "high" ring position or a "high" chamber configuration. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 6, diameter X is 0.47 in., diameter Y is 0.38 in., and distance Z is 0.29 in.

Figure 5:
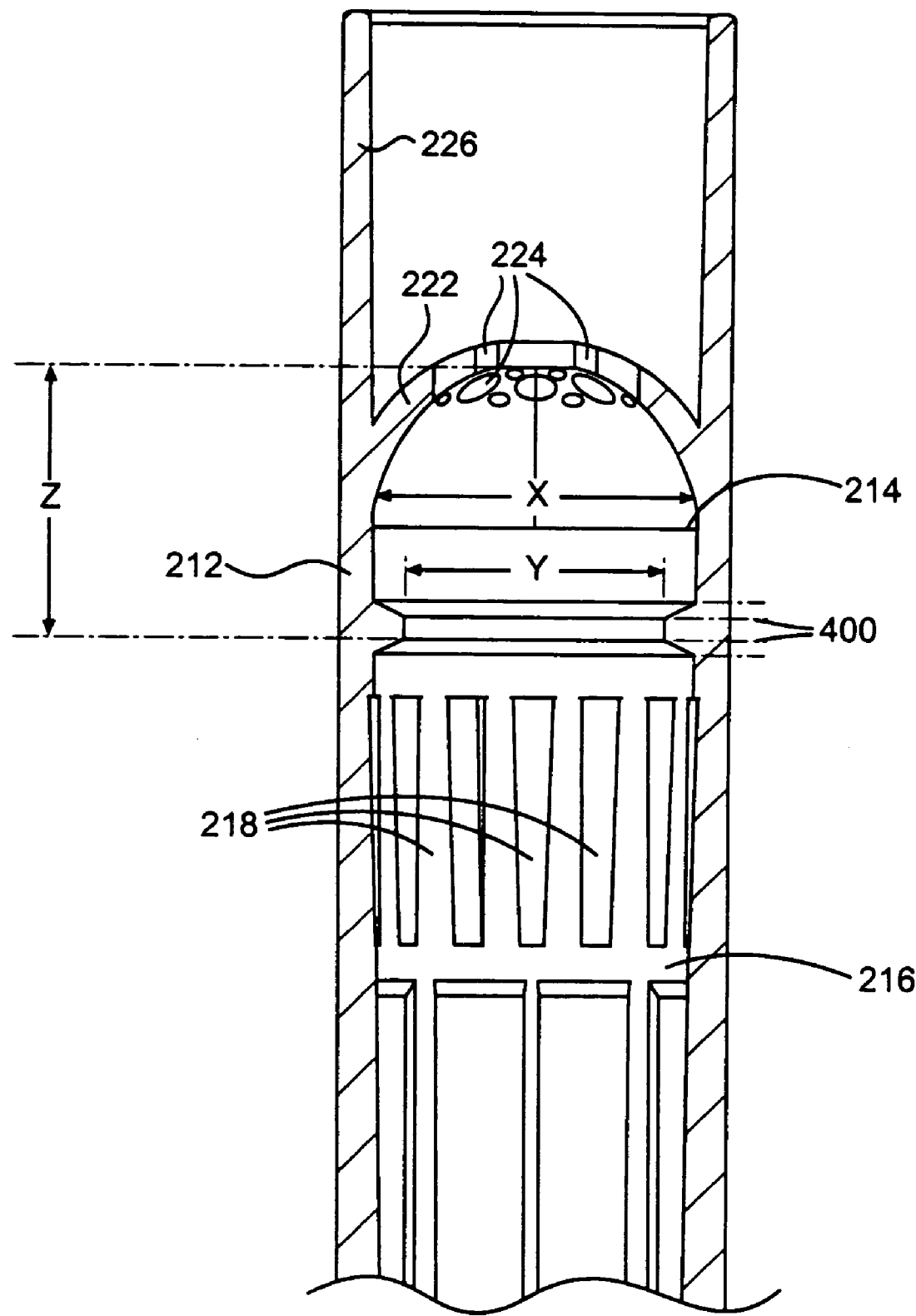
FIG. 5 is an enlarged partial cross-section of another embodiment of a dispersion chamber of the present invention showing another location for a ring in the dispersion chamber.

FIG. 5 is an enlarged partial cross-section of another embodiment of chamber 210. In the embodiment shown in FIG. 5, ring 400 is circumferentially coupled to an inner surface of chamber 210. An inner diameter of ring 400 is depicted as "Y", and is less than inner diameter X of chamber 210. In the embodiment shown in FIG. 5, ring 400 is disposed between the low ring position of FIG. 4 and the high ring position of FIG. 6. Such a configuration may be referred to herein as a "mid" ring position or "mid" chamber configuration. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 5, diameter X is 0.47 in., diameter Y is 0.38 in., and distance Z is 0.39 in.

In one embodiment of the present invention, ring 400 is integral with chamber 210. In such an embodiment, ring 400 and chamber 210 are formed as a unit, such as through an injection molding, extrusion or a casting process. In another embodiment of the present invention, ring 400 is attached to the inner surface of chamber 210 in a manner known to those skilled in the art, such as through the use of glue or other type of adhesive, or by using an attaching device such as a pin or screw, etc. Preferably, the casing of device 100 is made from a material that can be injection molded, such as a plastic material (preferably FDA approved, USP tested). As would be readily apparent to one skilled in the art, the material is preferably durable, easy to clean, and non-reactive with powder medicaments.

Figure 15:
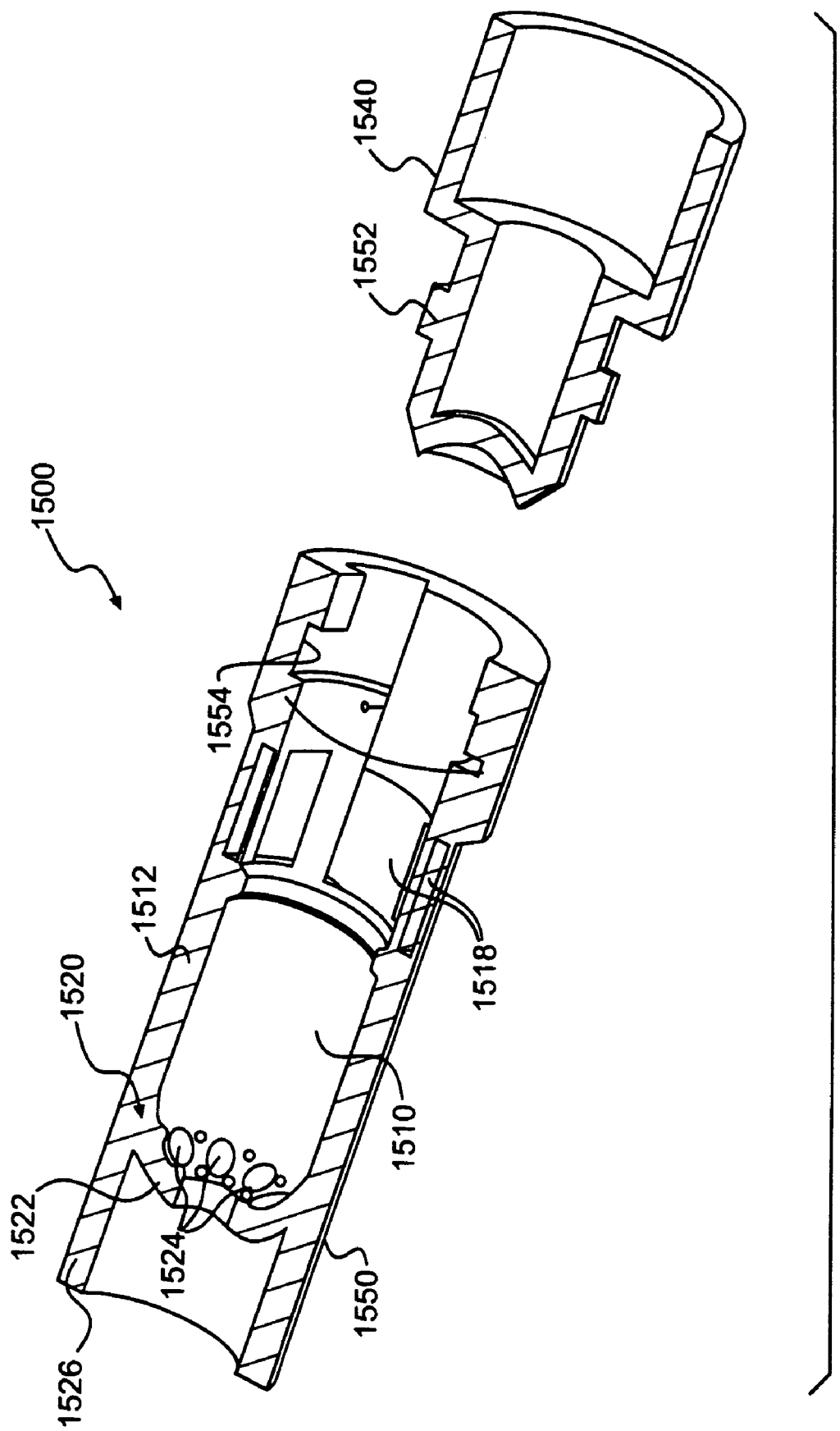
FIG. 15 is an exploded cross-sectional view of an alternate embodiment of a device of the present invention.

An exploded cross-sectional view of an alternate embodiment of a device 1500 of the present invention is shown in FIG. 15. Device 1500 includes a first or lower casing portion 1540 and a second or upper casing portion 1550 removably coupled to first casing portion 1540. First and second casing portions 1540 and 1550 are coupled through the use of a flange 1552 and a groove 1554. Preferred materials for device 1500 include Food and Drug Administration (FDA) approved, USP tested plastics. Preferably, device 1500 is manufactured using an injection molding process, the details of which would be readily apparent to one skilled in the art.

Device 1500 includes an inhalation or emitter portion 1520. Inhalation portion 1520 comprises a hemispheric region 1522 that defines a plurality of apertures 1524. It should be understood that the present invention is not limited to a particular number of apertures 1524, and can be configured such that at least one aperture 1524 is provided. An inhalation piece 1526 is provided to allow for inhalation of the medicament by a user. Inhalation piece 1526 can be configured as a mouth piece for inhalation through a user's mouth. Alternatively, inhalation piece 1526 can be configured as a nose piece for inhalation through a user's nose.

Device 1500 includes a cylindrical chamber 1510 that is defined by a straight wall 1512 of circular cross-section. A plurality of vents 1518 are defined by wall 1512, and are configured for introducing air into chamber 1510 to disperse powder released from, for example, capsule 219 as illustrated in FIG. 2. It should be understood that the present invention is not limited to a particular number of vents 1518, and can be configured such that at least one vent 1518 is provided. Powder released from capsule 219 is dispersed in chamber 1510 and inhaled through apertures 1524 and inhalation piece 1526 by the user.

As would be readily apparent to one skilled in the art, device 1500 can be configured with means for puncturing and means for biasing in a manner similar to that described above with respect to the embodiment shown in FIGS. 1 and 2. Means for puncturing are described in more detail below with respect to FIGS. 7A through 7D, 8, 9A-9B, 16A-16D, and 17A-17C. Moreover, device 1500 can be configured with the chamber designs described above with respect to FIGS. 3-6.

Figure 10:
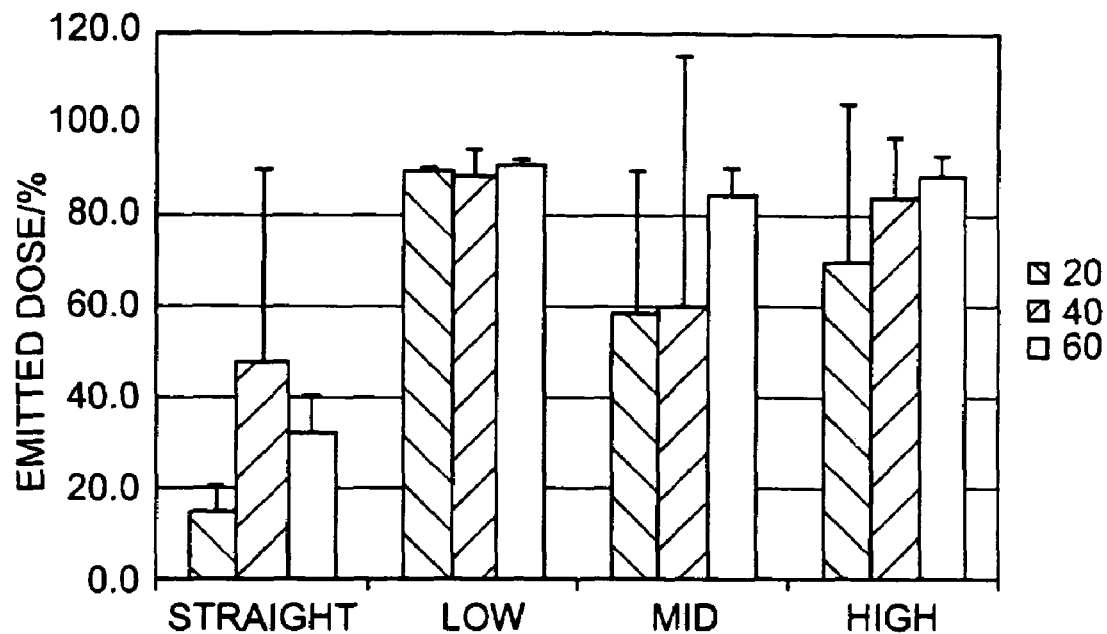
FIG. 10 is a bar graph illustrating emitted dose at peak inspiratory flow rates of 20 L/min (left bar), 40 L/min (center bar), and 60 L/min (right bar) for four dispersion chamber configuration.

FIG. 10 is a bar graph illustrating emitted dose at peak inspiratory flow rates of 20 L/min (left bar), 40 L/min (center bar), and 60 L/min (right bar) for a total volume of 2L for four dispersion chamber configurations (standard deviations shown; sample size n=3). The peak inspiratory flow rates were measured with a flow meter. The emitted dose measurement involved placing a capsule into four embodiments of the inhaler of the present invention for actuation into an emitted dose (ED) measurement apparatus. The ED apparatus included a powder filter and a filter holder. The powder collected by the ED apparatus was quantified by fluorescence spectrophotometry. The straight configuration is shown in FIG. 3; the low configuration is shown in FIG. 4; the mid configuration is shown in FIG. 5; and the high configuration is shown in FIG. 6. As can be seen from FIG. 10, each of the low, mid, and high configurations demonstrated a higher emitted dose at each of the three flow rates than the straight (no ring) configuration. Thus, the ring configuration of the present invention provides an improvement over conventional chamber designs without a ring, such as those shown in the '819 and '385 patents. At each of the flow rates shown in FIG. 10, the low configuration produced a higher emitted dose and a lower standard deviation than the mid and high configurations.

Figure 11:
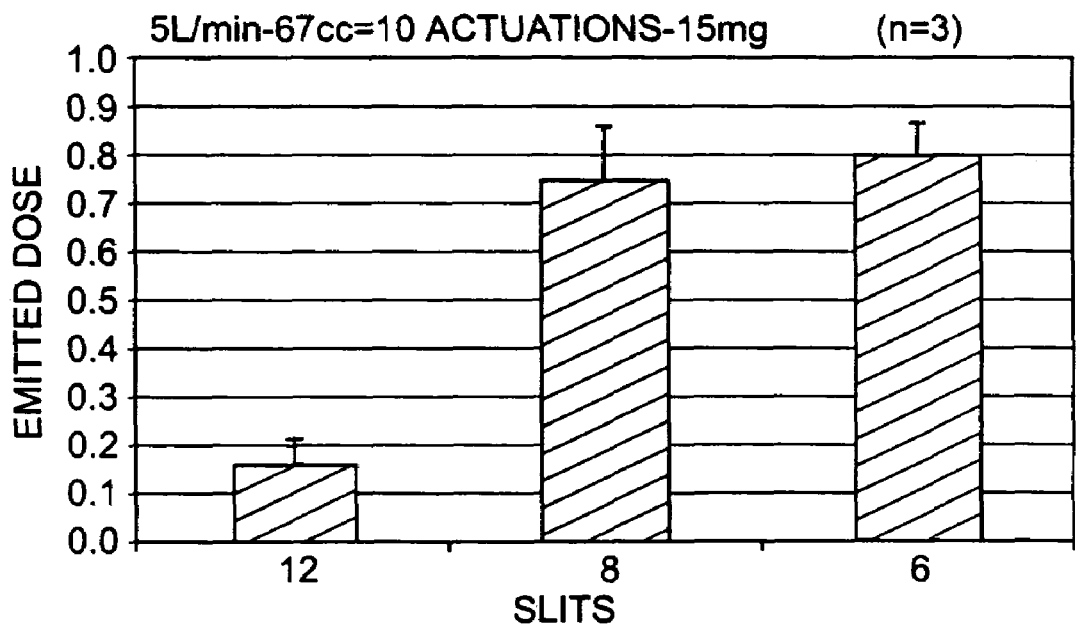
FIG. 11 is a bar graph illustrating emitted dose at low peak inspiratory flow rates for with varying numbers of vents.

FIG. 11 is a bar graph illustrating emitted dose at low peak inspiratory flow rates for devices with varying numbers of vents 218. The measurements were taken at a flow rate of 5 L/min, with a volume of 67 cc and a 15 mg dosage. As show in FIG. 11, by decreasing the number of vents 218, the emitted dose increases so that the device of the present invention successfully delivers a high emitted dose at a low peak inspiratory flow rate over multiple (ten) actuations. Thus, the device of the present invention achieves a high emitted dose at low peak inspiratory flow rates that is consistently reproducible with low standard deviation.

Figure 14:
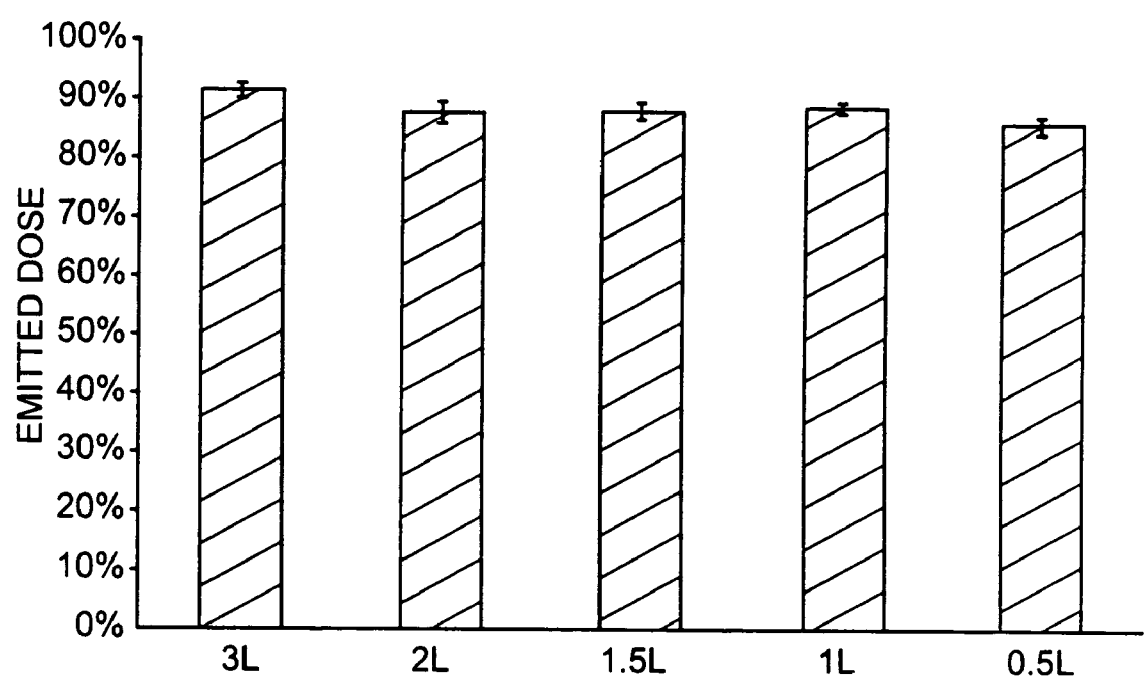
FIG. 14 is a bar graph illustrating the percentage emitted dose as a function of air volume.

Experiments were conducted to evaluate the emitted dose as a function of air volume drawn through the inhaler. The inhaler was operated at a constant flow rate of 30 L/min for a 5 mg dose. The volume of air through the inhaler was varied by varying the actuation time. Volumes of 0.5, 1.0, 1.5, 2.0 and 3.0 L were investigated. FIG. 14 shows the percentage emitted dose as a function of air volume (n=3, standard deviations shown). The emitted dose remained constant across the range of volumes and was consistently reproducible with low standard deviation.

In the embodiments having the inner diameter X of chamber 210 of 0.47 in and the inner diameter Y of ring 400 of 0.38 in., the ratio of the inner diameter of the ring to the inner diameter of the chamber is about 0.8. By modifying the inner diameters of the ring and the chamber, it is possible to optimize the emitted dose at varying flow rates. As reported in Annals of the ICRP, Human respiratory tract model for radiological protection, 24 (1-3), Elsevier Science, Inc., New York, 1994, the peak inspiratory flow rate for a tidal breathing seated adult male is 300 mL/s (18 L/min) for a volume of 750 mL. In one embodiment of a device of the present invention optimized for low peak inspiratory flow rates, inner diameter X of chamber 210 is 0.33 in and inner diameter Y of ring 400 is 0.30 in. In such an embodiment, the ratio of the inner diameter of the ring to the inner diameter of the chamber is about 0.9. Preferably, the ratio of the inner diameter of the ring to the inner diameter of the chamber is about 0.9 or less.

The device of the present invention can also be optimized for varying dosage ranges. One way to do so is to vary the dimensions of chamber 210 to accommodate varying sizes of capsules. For example, a chamber having an inner diameter X of 0.33 in.; inner diameter Y of 0.30 in., and distance Z of 0.57 in. can be used with size 2 and size 00 capsules. It should be readily apparent to one skilled in the art that chamber 210 can be scaled to accommodate varying capsule sizes, and to accommodate those capsule sizes at varying peak inspiratory flow rates.

Figure 12:
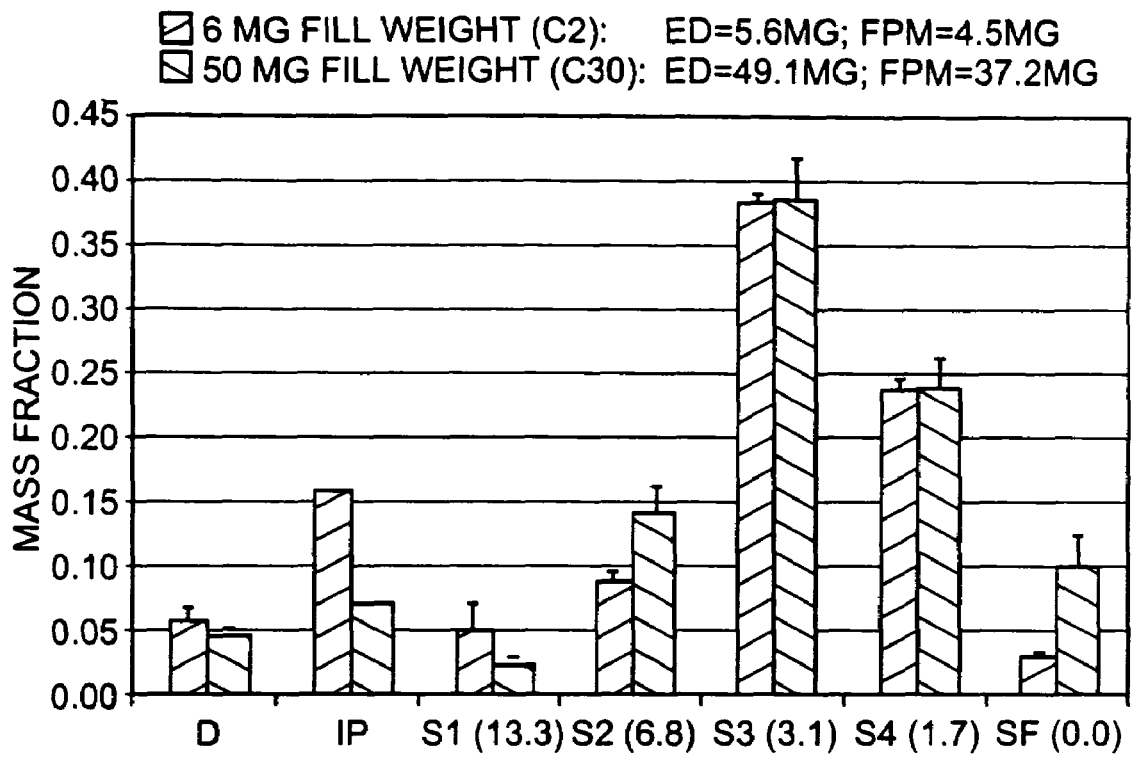
FIG. 12 is a bar graph showing a comparison of mass fraction distributions obtained for 6 mg (left bar) and 50 mg (right bar) fill weights.

The device of the present invention can be used with varying dosage ranges. A highly dispersible powder was prepared and loaded into capsules to obtain a large pre-metered dose (50 mg) and a smaller pre-metered dose (6 mg). The particle size characteristics of the powder were as follows: VMGD=10.6 μm; ρ=0.11 g/cc; and Da=3.5 μm, where VMGD is the volume mean geometric diameter, ρ is the powder density, and Da is the mean aerodynamic diameter. The aerodynamic particle size distributions were characterized using a multistage liquid impinger that extracted air at 60 L/min after actuating the inhaler device (D). As shown in FIG. 12, the mass fraction was measured at D, the induction port (IP) of the impactor, stages S1-S4, and the filter cutoff (SF). Size 2 capsules were used for the 6 mg dose and size 000 capsules were used for the 50 mg dose. FIG. 12 shows the results comparing the two particle size distributions obtained for the 6 mg (left bar) and 50 mg (right bar) doses. "ED" used on the graph refers to emitted dose, and FPM used on the graph refers to fine particle mass (estimate of the mass that would deposit in the lungs). The fine particle fraction <6.8 μm relative to the total dose ($FPF_{TD}$<6.8 μm) for the 6 and 50 mg doses were 74.4% and 75.0%, respectively. Similar aerodynamic particle size distributions were obtained for both doses.

Figure 13:
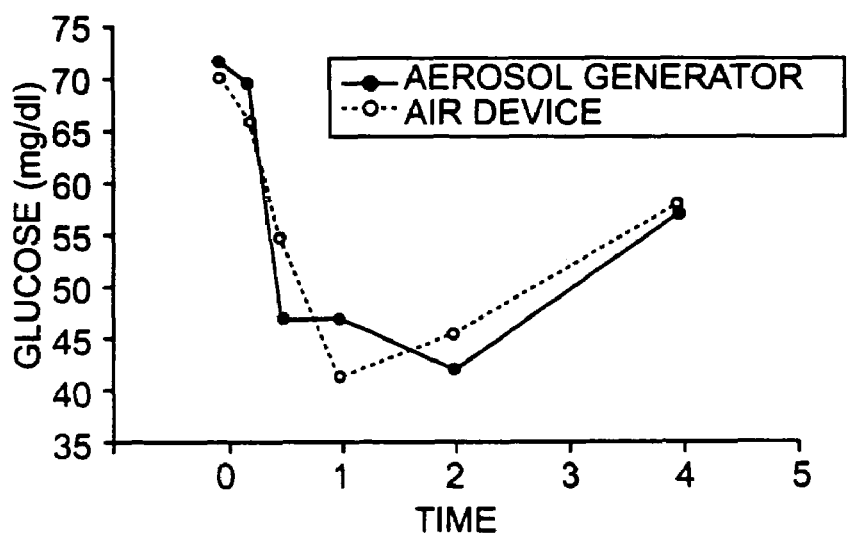
FIG. 13 is a graph showing glucose levels (mg/dL) in beagle dogs after administration of insulin using an aerosol generator and a device of the present invention with the low ring configuration substantially as shown in FIG. 4.

FIG. 13 is a graph showing glucose (mg/dL) in beagle dogs after administration of human insulin using an aerosol generator and a device of the present invention with the low ring configuration substantially as shown in FIG. 4. The generator is a device with proven ability for forming a respirable aerosol that results in deposition of powder in dog lungs. Metered powder is presented to a chamber where the powder is dispersed by a high velocity jet of air. The dispersed powder is directed toward a baffle to separate large agglomerates before inhalation by the dog. The pharmakodynamic profile shown in FIG. 13 confirms that the device of the present invention produces a pattern of powder deposition similar to the aerosol generator.

The dogs were anesthetized for the dosing procedure. A forced maneuver was used with dogs being ventilated at 75% of their vital capacity (approximately 100 cc/s or 6 L/min for a duration of 1 second). A 4 second breath-hold was applied at the end of each inhalation. A physically smaller device was used with the low ring configuration to facilitate administration. The device performed well at the low peak inspiratory flow rate with the anesthetized dogs using the forced maneuver. Based on these results, such a device could be used with a sleeping person or a person having breathing problems, such as from chronic obstructive pulmonary disease (COPD).

As can be seen from the description above, the device of the present invention relies upon the breath of the user to drive the inhalation process, yet the device is configured to work successfully at low peak inspiratory flow rates. As such, the device of the present invention has particular suitability for use with individuals who cannot breath hard, such as a child, an individual with respiratory disease, or individuals who are sleeping or in a coma.

The present invention further encompasses optimizing the configuration of device chamber 210 in order to maintain a low resistance of at most 0.28 $(cm\ H_2O)^{1/2}$/L/min and to achieve an emitted dose at least 85% when the receptacle contains a dose of up 10 to 50 mg of powder and when the device is operated at a peak inspiratory flow rate of 25 L/min or less and at an inhalation volume of 0.75 L or less. Experiments were performed on various chamber configurations, using size 00 capsules filled with a 20 mg dose of standard test powder. The various configurations were tested for emitted dose (ED), using known methods described above, at peak inspiratory flow rates ranging from 15 L/min to 25 L/min and at inhalation volumes ranging from 0.25 L/min to 0.75 L/min. In addition, the dispersion of the powder was quantified by measuring the volume mean geometric diameter (VMGD) of the emitted powder, by employing a RODOS dry powder disperser (or equivalent technique) such that at about 1 Bar, particles of the dry powder emitted from the RODOS orifice with geometric diameters, as measured by a HELOS or other laser diffraction system, are less than about 1.5 times the geometric particle size as measured at 4 Bar. In addition, the resistance of each chamber was measured using methods that will be apparent to one of ordinary skill in the art.

The following dimensions of chamber 210 were varied in order to discover the optimal combination: mouthpiece hole area, mouthpiece hole number, chamber diameter (X in FIG. 4), ring diameter (Y in FIG. 4), vent area (the product of vent width, vent height, and vent number), and capsule hole area (the product of the hole area and the number of holes). Initially, it was discovered that it is always desirable to maximize the capsule hole area. Accordingly, the capsule hole area was fixed at 0.013 square inches. It should be understood that the present invention encompasses other capsule hole areas, especially when used with different sized capsules. It was also determined that the total area of the holes in the mouthpiece was an important factor but that the number of holes in the mouthpiece did not effect the results.

Next, 130 chambers were tested, each having a different combination of mouthpiece hole area, chamber diameter, ring diameter, and vent area. During the testing it was discovered that each of these dimensions have competing effects on the emitted dose, the volume mean geometric diameter, and the resistance of the chamber. For example, increasing the vent area has a positive impact on (i.e., decreases) resistance, but has a negative effect on (i.e., decreases) emitted dose and has a negative effect on (i.e., increases) volume mean geometric diameter. Other dimensions have similar competing effects. In addition, as shown in FIGS. 20A to 20C and discussed in detail below, the vent area and the chamber diameter have combinational effects on the properties of the chamber. Other combinations of dimensions have similar combinational effects.

Of the 130 chambers tested, three preferred embodiments of chambers were identified that achieved the desired characteristics. The pertinent dimensions of each of those chambers is described in Table 1.

TABLE 1

Aspects of Preferred Embodiments of Chambers

|  | Chamber F | Chamber H | Chamber I |
|---|---|---|---|
| Resistance (cm $H_2O)^{1/2}$/L/min | 0.27 | 0.22 | 0.19 |
| Mouthpiece Hole Area (sq. in.) | 0.020 | 0.022 | 0.022 |
| Chamber Diameter (in.) | 0.440 | 0.436 | 0.440 |
| Ring Diameter (in.) | 0.400 | 0.380 | 0.400 |
| Vent Area (sq. in.) | 0.014 | 0.020 | 0.024 |
| Vent Number (in.) | 3 | 4 | 5 |
| Vent Width (in.) | 0.020 | 0.025 | 0.020 |
| Vent Length (in.) | 0.236 | 0.195 | 0.236 |

Tables 2-4 summarize the emitted dose (ED) (in percent) and dispersion (volume mean geometric diameter (VMGD) in microns)) (with standard deviations in parentheses) achieved with each of these preferred embodiments of chambers, operated with a capsule having a dose of approximately 20 mg and at peak inspiratory flow rates from 15 L/min to 25 L/min and at inhalation volumes from 0.25 L to 0.75 L. The test powder, referred to herein as "standard test powder," was a placebo powder of 84.99 wt % maltodextran, 15 wt % leucine, and 0.01 wt % rhodamine. It had a VMGD of 12 μm measured using the RODOS at 1 bar and an aerodynamic size (volume mean aerodynamic diameter or VMAD) of 3 μm measured using an 8 stage Anderson Cascade Impactor. The goal emitted dose was at least 85%. The goal dispersion for the standard test powder was a VMGD of 11.8 μm or less, although it should be understood that this goal would vary depending on the type of powder used.

TABLE 2

Chamber F

| Volume → | 0.25 L | | 0.5 L | | 0.75 L | |
|---|---|---|---|---|---|---|
| Flow Rate | VMGD | ED | VMGD | ED | VMGD | ED |
| 15 L/min | 15.0 | 67 | 13.5 | 87 | 16.4 | 93 |
| | (0.8) | (14) | (0.8) | (6) | (1.6) | (3) |
| 20 L/min | 10.2 | 66 | 9.3 | 89 | 9.0 | 88 |
| | (0.5) | (9) | *(0.6)* | *(4)* | *(0.6)* | *(10)* |
| 25 L/min | 9.3 | 77 | *7.8* | *91* | *7.9* | *93* |
| | (0.6) | (8) | *(0.3)* | *(5)* | *(0.5)* | *(3)* |

TABLE 3

Chamber H

| Volume → | 0.25 L | | 0.5 L | | 0.75 L | |
|---|---|---|---|---|---|---|
| Flow Rate | VMGD | ED | VMGD | ED | VMGD | ED |
| 15 L/min | 16.1 | 57 | 15.7 | 78 | 14.6 | 90 |
| | (0.8) | (9) | (0.7) | (11) | (1.1) | (4) |
| 20 L/min | 12.0 | 66 | 10.4 | 81 | *10.2* | *89* |
| | (0.6) | (9) | (0.6) | (7) | *(0.4)* | *(8)* |
| 25 L/min | 10.4 | 75 | *8.1* | *94* | *8.2* | *97* |
| | (0.6) | (11) | *(0.3)* | *(4)* | *(0.3)* | *(1)* |

TABLE 4

Chamber I

| Volume → | 0.25 L | | 0.5 L | | 0.75 L | |
|---|---|---|---|---|---|---|
| Flow Rate | VMGD | ED | VMGD | ED | VMGD | ED |
| 15 L/min | 18.2 | 49 | 19.3 | 69 | 18.2 | 79 |
| | (0.7) | (8) | (1.3) | (12) | (1.9) | (12) |
| 20 L/min | 13.4 | 43 | 12.7 | 71 | 12.5 | 83 |
| | (0.5) | (13) | (1.0) | (10) | (0.6) | (9) |
| 25 L/min | 12.0 | 65 | *10.0* | *85* | *9.7* | *87* |
| | (0.4) | (8) | *(0.4)* | *(7)* | *(0.3)* | *(9)* |

In Tables 2-4, the italicized print indicates peak inspiratory flow rates and inhalation volumes at which the chambers achieved both the goal of an emitted dose of at least 85% and a dispersion of a VMGD of 11.8 μm or less. As is apparent from Tables 2-4, these goals were achieved for peak inspiratory flow rates of 25 L/min or less and for inhalation volumes of 0.75 L or less. Moreover, the standard deviations were quite small for the emitted dose (on the order of approximately 10% or less) and for the VMGD (on the order of approximately 1.0 or less).

In addition, statistical analysis was used to extrapolate the results from these three chambers into ranges of variables that would consistently yield the desired emitted dose and volume mean geometric diameter. For example, optimized combinations of chamber diameter, vent area, and mouthpiece hole area were determined. It should be apparent to one of ordinary skill in the art that optimization analysis could be performed for other variable combinations, and for other capsule sizes and powders, in order to optimize the design of the chambers.

Having done a thorough analysis, it has been determined that the present invention encompasses an optimized chamber, for a size 00 capsule, that has:

at least one aperture has an aggregate area of 0.018 to 0.022 square inches; or
a ring inner diameter of 0.380 to 0.400 inches; or
a chamber inner diameter of 0.400 to 0.440 inches; or
three to five vents; or
a vent width of 0.020 to 0.025 inches; or
a vent length of 0.195 to 0.236 inches; or
a total vent area of 0.014 to 0.024 square inches, and that when used with a dose of approximately 20 mg of the standard test powder described above and operated at a peak inspiratory flow rate of 25 L/min or less and an inhalation volume of 0.75 L or less, the emitted dose of powder will be at least 85%, and the VMGD will be about 11.8 μm or less.

While the preferred embodiment described above relates to optimizing the design of a chamber to have a have a resistance of at most 0.28 (cm $H_2O)^{1/2}$/L/min and to provide an emitted dose of at least 85% when the dose of standard test powder is about 20 mg and when the device is operated at a peak inspiratory flow rate of 25 L/min or less and at an inhalation volume of 0.75 L or less, it should be understood that the invention also encompasses optimizing the chamber to have any other combination of resistance and emitted dose, at any other combination of powder type, dose weight, peak inspiratory flow rate, and inhalation volume.

Figure 7A:
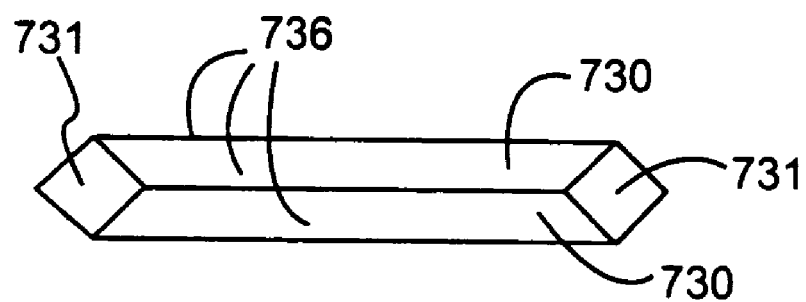
FIG. 7A is a top view of a preferred embodiment of a staple suitable for use with the device of the present invention.
Figure 7B:
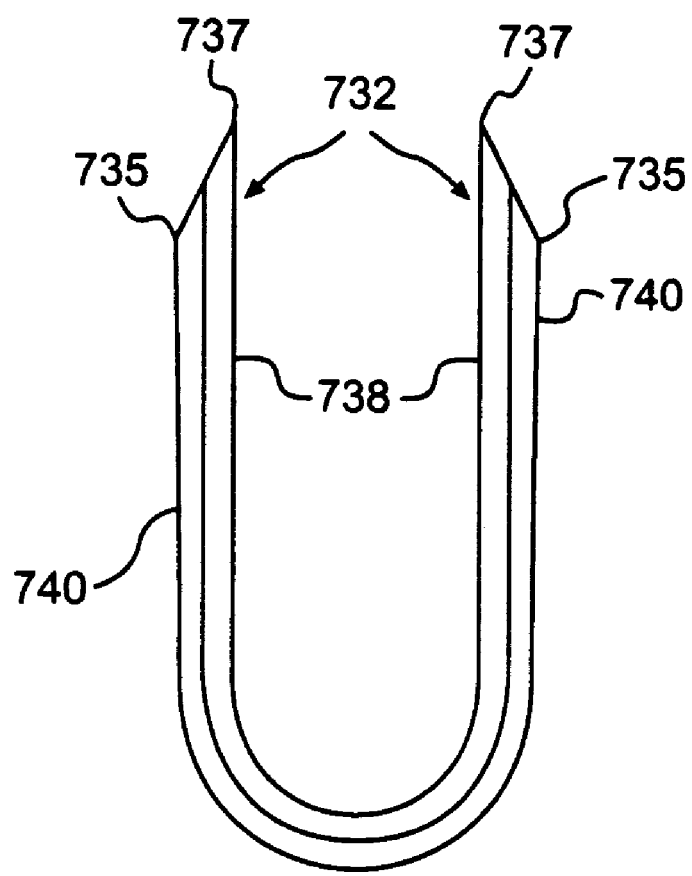
FIG. 7B is a front view of the embodiment shown in FIG. 7A.
Figure 7C:
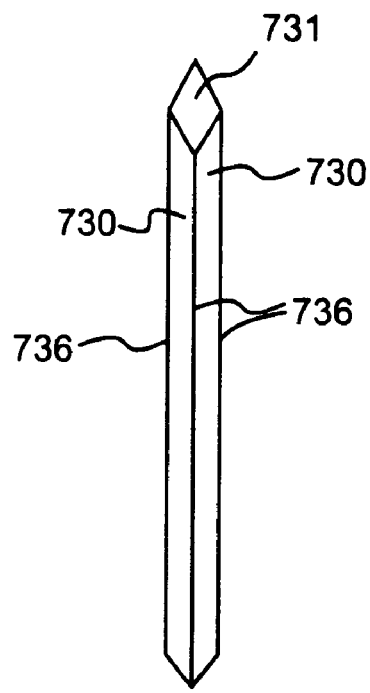
FIG. 7C is a side view of the embodiment shown in FIG. 7A.
Figure 7D:
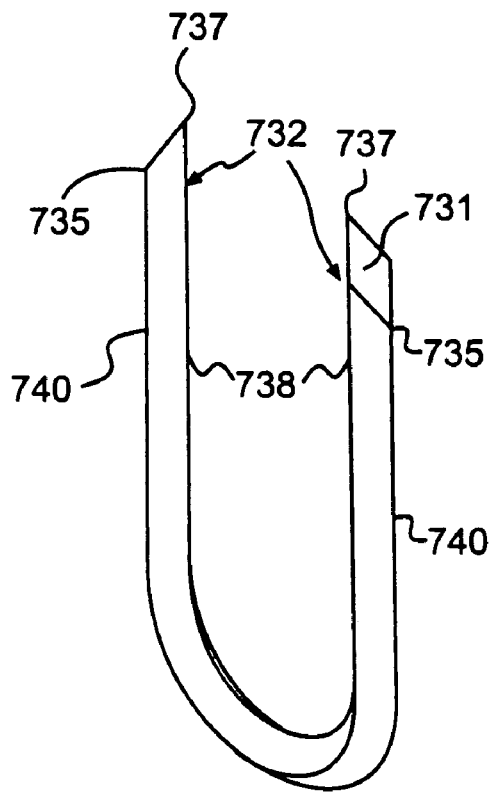
FIG. 7D is an isometric view of the embodiment shown in FIG. 7A.

Turning now to FIGS. 7A through 7D, a preferred embodiment of the means for puncturing, in the form of a staple, suitable for use in the present invention is shown. The staple preferably comprises a rectangular length of material that has four planar side surfaces 730. Each planar side surface intersects with two other planar side surfaces to create a total of four non-planar edges 736. The staple is preferably bent into a substantially U-shaped configuration, thereby having a rounded portion and two prongs 732. The prongs 732 terminate at two end surfaces 731. As best seen in FIGS. 7A, 7C and 7D, end surfaces 731 are diamond-shaped.

The diamond-shaped end surfaces are created by bending the material about a non-planar edge. This configuration is best shown in FIGS. 7B and 7D. As can be seen, each prong 732 has an inner surface 738 that comprises one of the non-planar edges and an outer surface 740 that comprises the opposite non-planar edge. The inner surface 738 of each prong 732 terminates at the uppermost portion 737 of the diamond-shaped end surface, thereby creating a cutting edge for the prong. The outer surface 740 of the prong 732 terminates at the lowermost portion 735 of the diamond-shaped end surface.

Figure 9A:
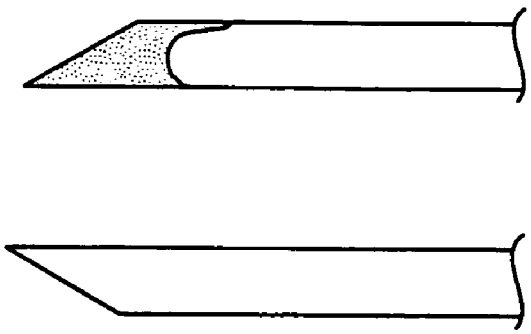
FIG. 9A shows a partial view of another embodiment of a staple suitable for use with the device of the present invention.
Figure 9B:
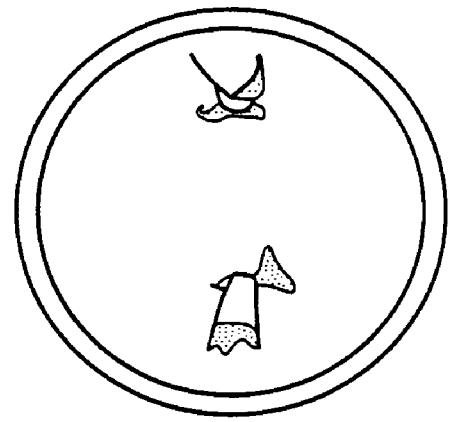
FIG. 9B illustrates the puncture obtained with the staple shown in FIG. 9A.

FIGS. 9A and 9B depict another embodiment of a means for puncturing in the form of a staple, suitable for use in the present invention. This staple preferably comprises a rectangular length of material that has four planar side surfaces. Each planar side surface intersects with two other planar side surfaces to create a total of four non-planar edges. The staple is preferably bent into a substantially U-shaped configuration, thereby having a rounded portion and two prongs. The prongs terminate at two end surfaces that have a square shape.

The square-shaped end surfaces are created by bending the material about a planar side surface. As shown in FIG. 9A, each prong has an inner surface that comprises one of the planar side surfaces and an outer surface that comprises the opposite planar side surface. The inner surface of each prong terminates at the uppermost portion of the square-shaped end surface, thereby creating a cutting edge for the prong. The outer surface of the prong terminates at the lowermost portion of the square-shaped end surface.

FIG. 9B illustrates a puncture obtained from using the staple depicted in FIG. 9A. As shown, the holes formed by this staple have the appearance of being cut with a sharp edge. In addition, the material removed to create the hole is peeled back and remains well attached to the capsule; thereby preventing the capsule material from being inhaled by the user when the powder medicament is being dispensed.

Figure 8:
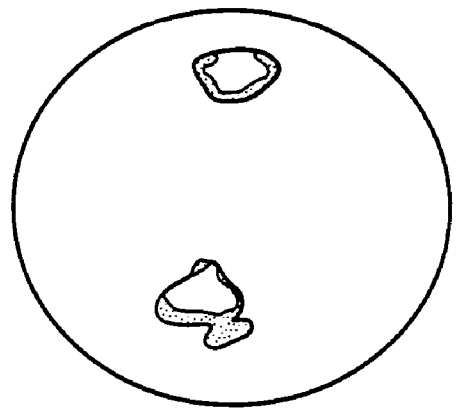
FIG. 8 shows the puncture obtained with the staple shown in FIGS. 7A through 7D.

FIG. 8 illustrates a puncture obtained from using the staple depicted in FIGS. 7A-7D. The holes formed by the staple appear to be cut with a sharp edge, and the excess material is peeled back. In testing, the effort required to puncture the capsule is lower than circular section staples, and approximately the same as a square section staple. However, during testing, no instances were noted of crushed or otherwise mispunctured capsules. These staples are extremely inexpensive to produce, approximately one-third the cost of square section staples such as those depicted in FIG. 9A.

In addition to improved puncturing performance, drug delivery from capsules punctured with the staple depicted in FIGS. 7A-7D is greatly improved. The Emitted Dose (ED) and Fine Particle Fraction (FPF) of a test powder was measured at both 20 and 60 Liters per minute (LPM). In all cases, the aerosol emitted from capsules punctured with the diamond section staple of FIGS. 7A-7D was improved over a conventional circular stock staple. Most significantly, the FPF of powder delivered at 20 liters per minute was improved almost to the level of the FPF at 60 liters per minute.

FIGS. 16A through 16D illustrate yet another preferred embodiment of a means for puncturing suitable for use in the present invention, in the form of puncturing device 1600. Puncturing device 1600 comprises two substantially longitudinal prongs 1620 coupled to a base 1610 coupled to form a U-shape. Base 1610 is configured to be coupled to inhalation device 100. Although two prongs are illustrated in the figures, it should be understood that any number of prongs 1620 could be coupled to base 1610, depending on the number of holes desired to be made in the receptacle. For ease of discussion, only one of prongs 1620 is described in detail below.

Prong 1620 has a proximal end coupled to the base 1610 and a distal end having a puncturing surface 1630 for making an initial puncture hole in the receptacle. In the embodiment shown, puncturing surface 1630 is a sharp point, although it should be understood that puncturing surface 1630 may also have a different shape, such as a sharp edge.

The periphery of prong 1620 further comprises a primary cutting edge 1640 running from the proximal end to the distal end of prong 1620 and terminating at puncturing surface 1630. In a preferred embodiment, primary cutting edge 1640 is sharp and may have additional features to enhance its cutting ability, such as being serrated or jagged. The periphery also comprises substantially planar face 1650 running from the proximal end to the distal end of prong 1620. In a preferred embodiment substantially planar face 1650 is substantially flat, although it may also be another suitable shape, such as slightly concave.

Prong 1620 further comprises a plurality of longitudinal edges 1645 and a plurality of longitudinal faces 1655 disposed around the periphery and running from the proximal end to the distal end of the prong. In a preferred embodiment, each of the longitudinal faces 1655 is substantially planar, although it should be understood that they may be other suitable shapes, such as concave. In a preferred embodiment, each of the longitudinal edges 1645 is sharp, although it should be understood that they may also have other suitable shapes, such as being serrated, jagged, blunt, or rounded.

In the embodiment shown in FIG. 16D, there are four longitudinal edges 1645 and four longitudinal faces 1655, in addition to primary cutting edge 1640 and substantially planar face 1650, so that prong 1620 has a cross section substantially in the shape of a pentagon. However, it should be understood that there may be any number and arrangement of longitudinal faces 1655 and longitudinal edges 1645 so that prong 1620 may have other suitable cross sectional shapes, so long as substantially planar face 1650 is opposite to primary cutting edge 1640. For example, width W (see FIG. 16D) of substantially planar face 1650 may be very small and the four longitudinal faces 1655 may be substantially at right angles to each other so that prong 1620 has substantially a diamond shaped cross section. In yet another embodiment, prong 1620 may have two longitudinal edges 1645 and two longitudinal faces 1655, in addition to primary cutting edge 1640 and substantially planar face 1650, so that prong 1620 has a triangular cross section.

The distal end of prong 1620 preferably further comprises an angled face 1660 terminating in puncturing surface 1630 at its distal end and at substantially planar face 1650 at its proximal end, as best seen in FIG. 16C. It should be understood that angled face 1660 may be at any angle, or may be comprised of a plurality of angled faces at various angles, so long as puncturing surface 1630 is located distal to the distal end of substantially planar face 1650.

Figure 16A:
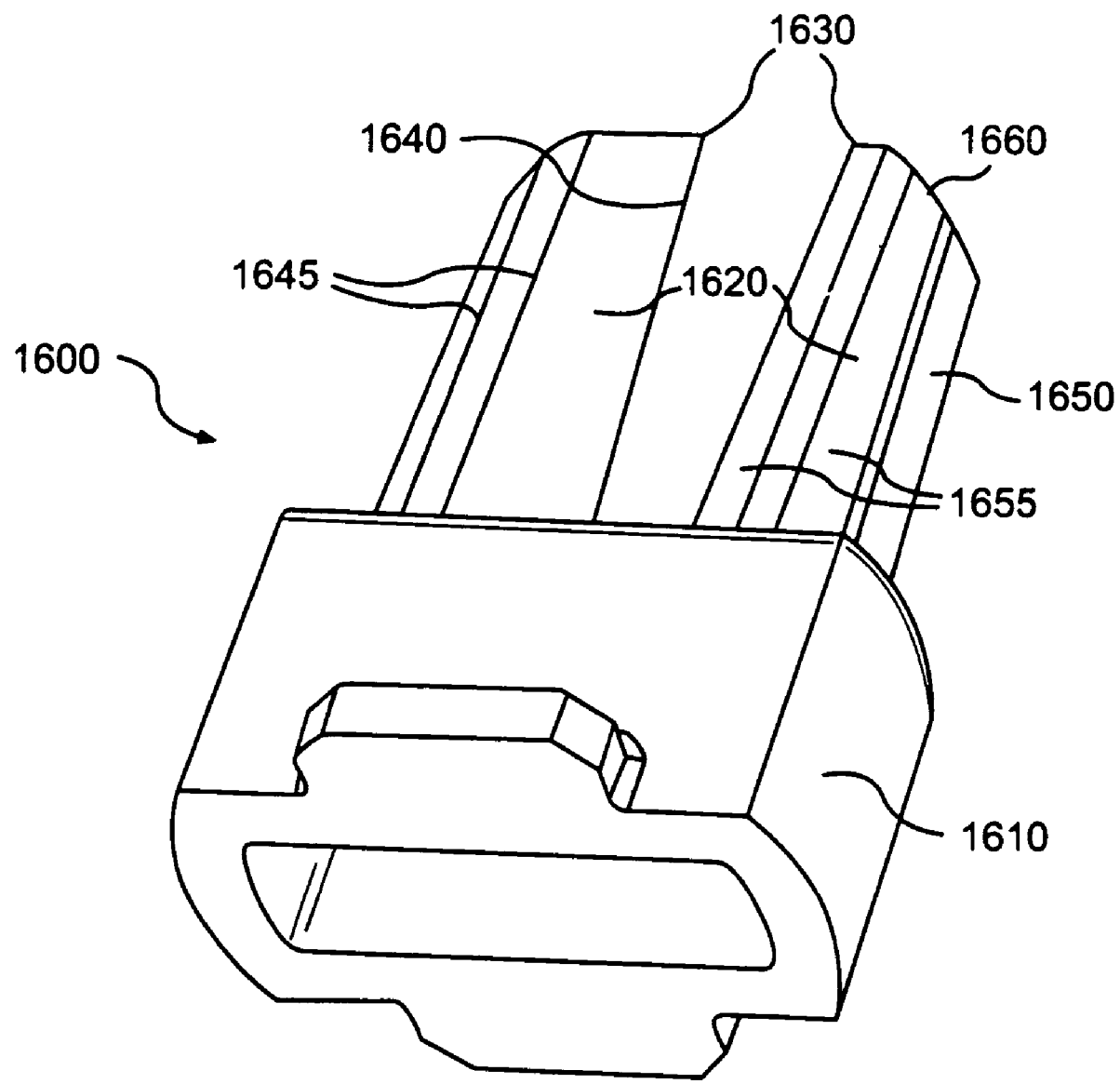
FIG. 16A is a perspective view of an alternative embodiment of a puncturing device suitable for use with the present invention.
Figure 16B:
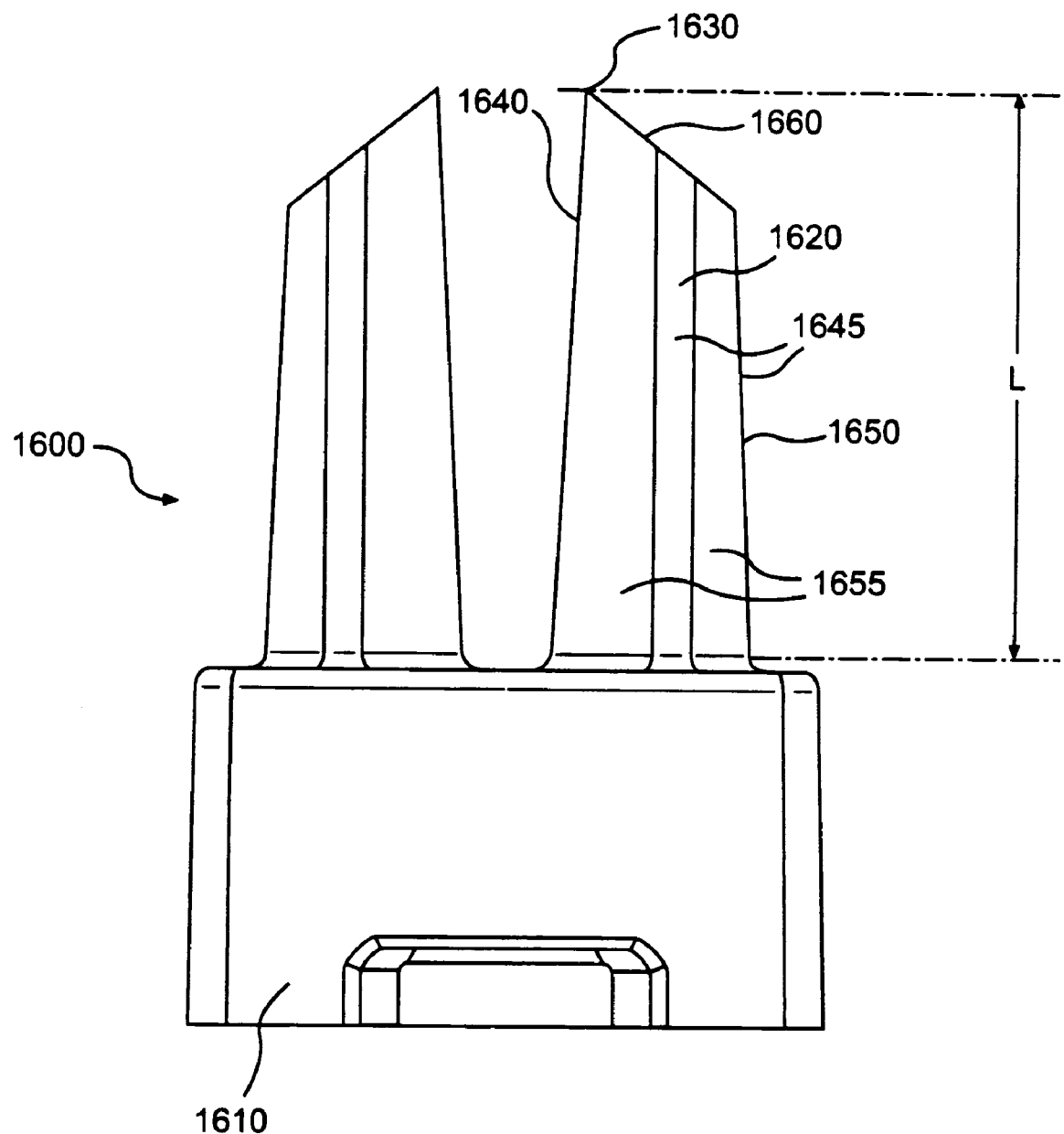
FIG. 16B is a front view of the puncturing device shown in FIG. 16A.
Figure 16C:
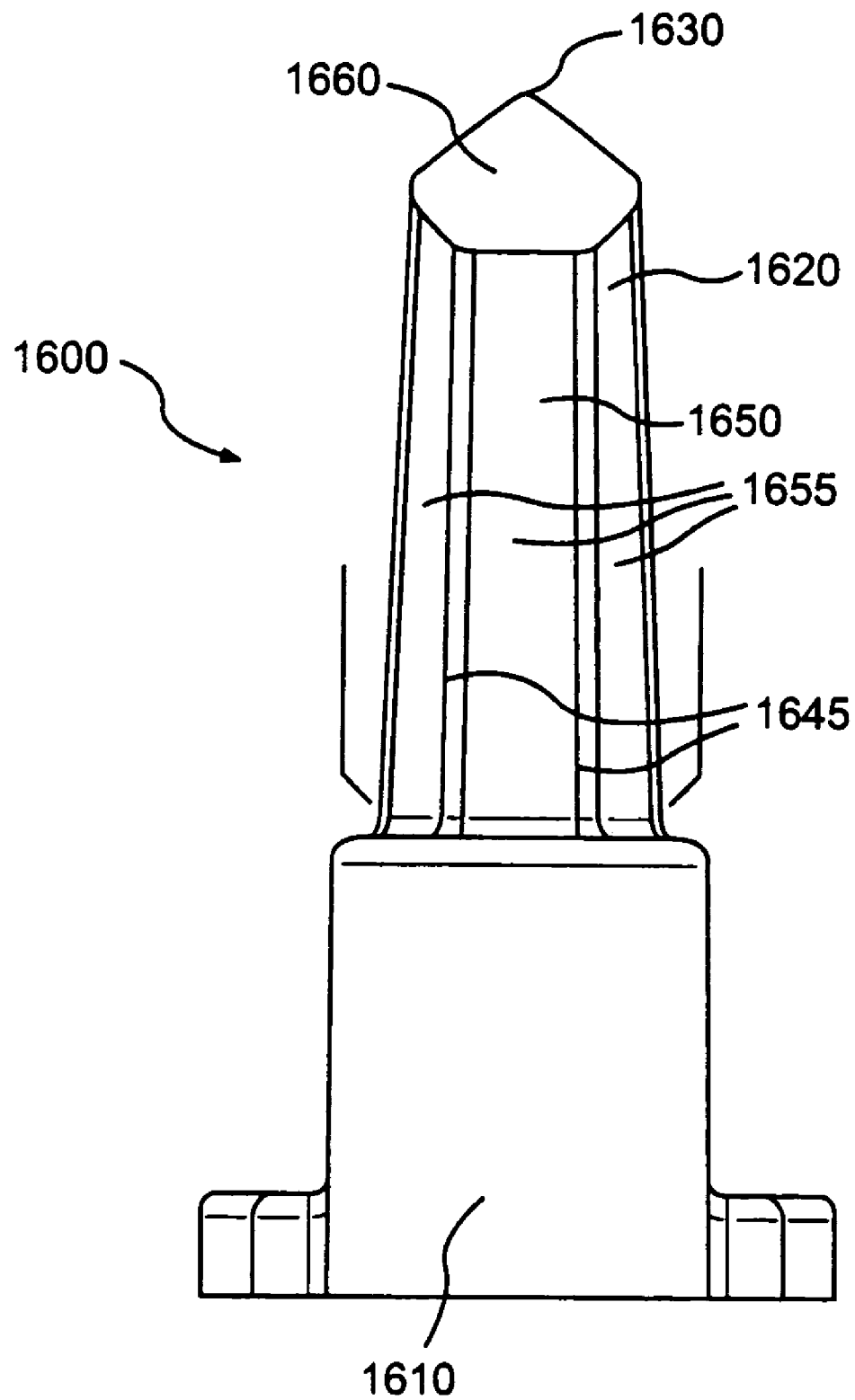
FIG. 16C is a side view of the puncturing device shown in FIG. 16A.
Figure 16D:
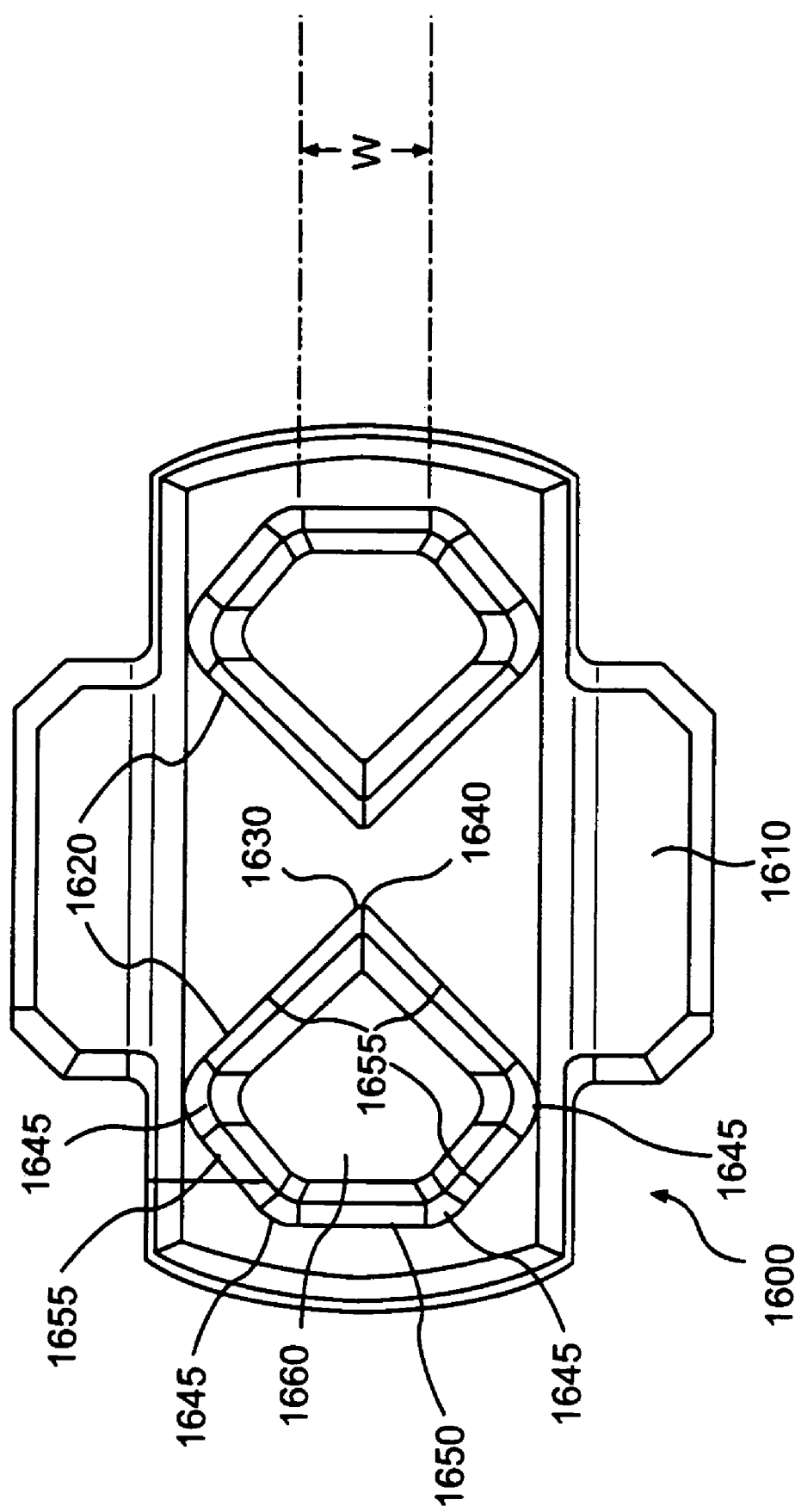
FIG. 16D is a top view of the puncturing device shown in FIG. 16A.

Also, as shown in FIG. 16B, prong 1620 is slightly tapered so that the distal end is smaller than the proximal end. This tapering facilitates removing prong 1620 from the wall to be punctured without sticking and without detaching the chad formed in the wall. In a preferred embodiment, the angle of the taper is approximately 0.116 degrees with respect to a longitudinal axis of the prong.

In a preferred embodiment, puncturing device 1600 is made by injection molding of a suitable metal, such as stainless steel or titanium. Injection molding facilitates making larger prongs than could be achieved in conventional piercing devices. As discussed above, larger prongs facilitate making larger holes in the receptacle in order to optimize the emitted dose and the volume mean geometric diameter. It should be understood that puncturing device 1600 may be made of another material, such as ceramic or plastic, or by another manufacturing process, such as casting or forging. Moreover, it should be understood that the other embodiments of means for puncturing 230 depicted in FIGS. 7A-D and 9A-B could be made by any of these manufacturing processes or materials. It should also be understood that these other embodiments of means for puncturing 230 could be coupled to a base similar to base 1610 in FIGS. 16A-D.

Figure 17A:
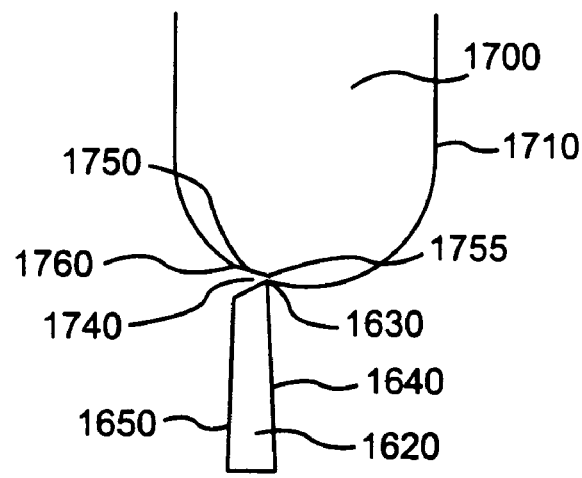
FIGS. 17A-17C are schematic diagrams of one of the prongs of the puncturing device shown in FIGS. 16A-D being used to puncture a receptacle and create a hanging chad therein.
Figure 17B:
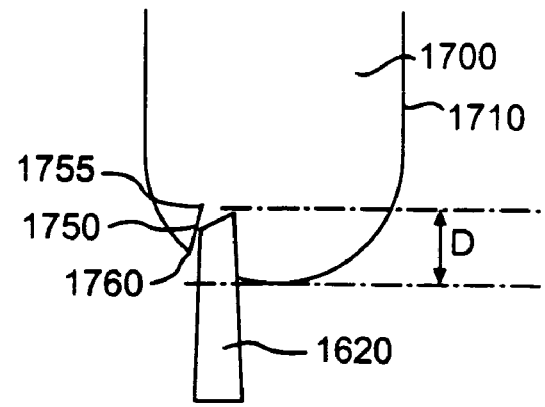
Figure 17C:
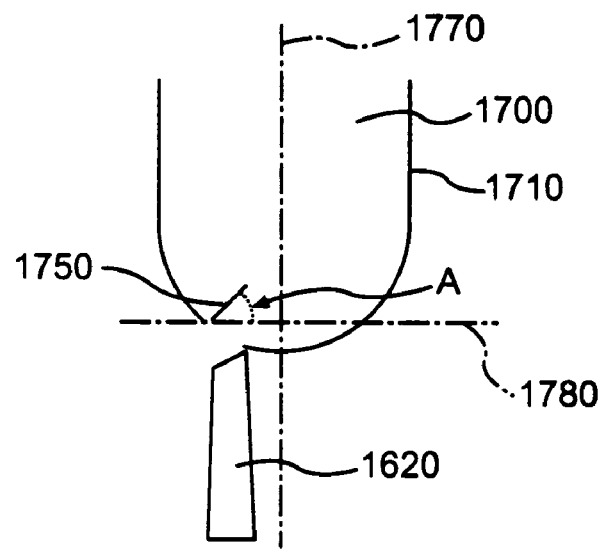

FIGS. 17A through 17C schematically illustrate the use of prong 1620 to puncture and create a hanging chad in the wall 1710 of receptacle 1700. Although receptacle 1700 is illustrated in the shape of a capsule, it should be understood that the receptacle may have any other suitable shape, such as a tablet or a blister pack. Receptacle 1700 has a longitudinal axis 1770 substantially parallel to prong 1620 and a minor axis 1780 substantially perpendicular to longitudinal axis 1770.

As shown in FIG. 17A, puncturing surface 1630 of prong 1620 initially punctures a small opening 1740 in wall 1710. Next, as shown in FIG. 17B, prong 1620 is inserted into receptacle 1700 to a depth D, increasing the size of opening 1740 and forming chad 1750 having free end 1755. Substantially planar face 1650 forms a hinge 1760 between chad 1750 and wall 1710 so that chad 1750 is a hanging chad. Finally, as shown in FIG. 17C, prong 1620 is withdrawn from wall 1710, leaving hanging chad 1750 inside of receptacle 1700. Preferably, the angle A between chad 1750 and minor axis 1780, after prong 1620 has been removed from receptacle 1700, is at least 30 to 45 degrees in order to facilitate efficient emptying of the receptacle and a high emitted dose.

Several experiments were performed to evaluate the emitted doses achieved using puncturing device 1600. The tests were done with size 00 capsules containing approximately 20 mg per capsule and using a flow rate of approximately 20 L/min for 1.5 seconds.

In the first experiment, two prototype staples similar in shape to the U-shaped staple shown in FIGS. 7A-7D but with larger prongs (referred herein as Staple #1 and Staple #2) were used to puncture ten capsules. For Staple #1, the mean emitted dose from the punctured capsules was approximately 81.0%, with a standard deviation of approximately 13.3%. For Staple #2, the mean emitted dose was approximately 51.0%, with a standard deviation of approximately 25.3%.

Next, the same experiments were run with Staple #1 and Staple #2, only this time the chads were manually opened to an angle of at least 45 degrees with respect to the receptacle after removal of the puncturing device, by using a blunt instrument. In that case, the mean emitted dose for Staple #1 was approximately 93.6%, with a standard deviation of approximately 2.4%. For Staple #2, the mean emitted dose was approximately 93.0%, with a standard deviation of approximately 2.0%.

The same experiments were then run using a prototype of the puncturing device 1600 illustrated in FIGS. 16A-D (called Staple #4). In the experiment performed without manually opening the chads to an angle of at least 45 degrees, the mean emitted dose after using Staple #4 was approximately 89.5%, with a standard deviation of approximately 4.9%. In the experiment in which the hanging chads were manually opened to an angle of at least 45 degrees, the mean emitted dose was approximately 93.9%, with a standard deviation of approximately 1.8%. By itself, Staple #4 opens the hanging chad to an angle of at least 30 to 45 degrees. Thus, the embodiment of puncturing device 1600 illustrated in FIGS. 16A-D has significant advantages over other puncturing means, including those previously described in this application, because it yields a consistent emitted dose of at least 85% and opens the chads to an angle of at least 30 to 45 degrees.

Other experiments were performed to determine the puncturing depth that could be achieved using puncturing device 1600. First, Staple #3, another prototype having almost the same structure as Staples #1 and #2, was used to puncture capsules to varying depths. It was determined that the capsules could consistently be punctured to a depth of 0.1495 inches without causing chads to become removed. Next, Staple #5, another prototype of puncturing device 1600 illustrated in FIGS. 16A-D, was used to puncture capsules to varying depths. It was determined that the prongs could be inserted to a depth of at least ¾ of the length L (see FIG. 16B) of the prongs, or approximately 0.2442 inches, without causing the chads to become removed. Accordingly, puncturing device 1600 illustrated in FIGS. 16A-D has significant advantages over other puncturing means because it allows greater depth of puncturing, which allows for greater optimization of the inhaler.

The present invention also relates to a method for dispensing powder medicaments to a user through the various embodiments of the disclosed inhalation device. In such a method, a receptacle containing the powder medicament, e.g., a capsule 219, is placed or formed into cylindrical chamber 210. When the user compresses the inhalation device, staple 230 is moved toward capsule 219 thereby puncturing capsule 219 to cause the release of powder into chamber 210. After release into the chamber, the powder is then inhaled by the user through apertures 224 and inhalation piece 226. As noted, inhalation piece 226, can be configured as either a mouth piece or a nose piece. For subsequent uses, the user merely replaces emptied capsule 219 with another capsule 219 that contains a new supply of power medicament. Alternatively, powder medicament is injected into a permanent receptacle that is formed into chamber 210.

Figure 18:
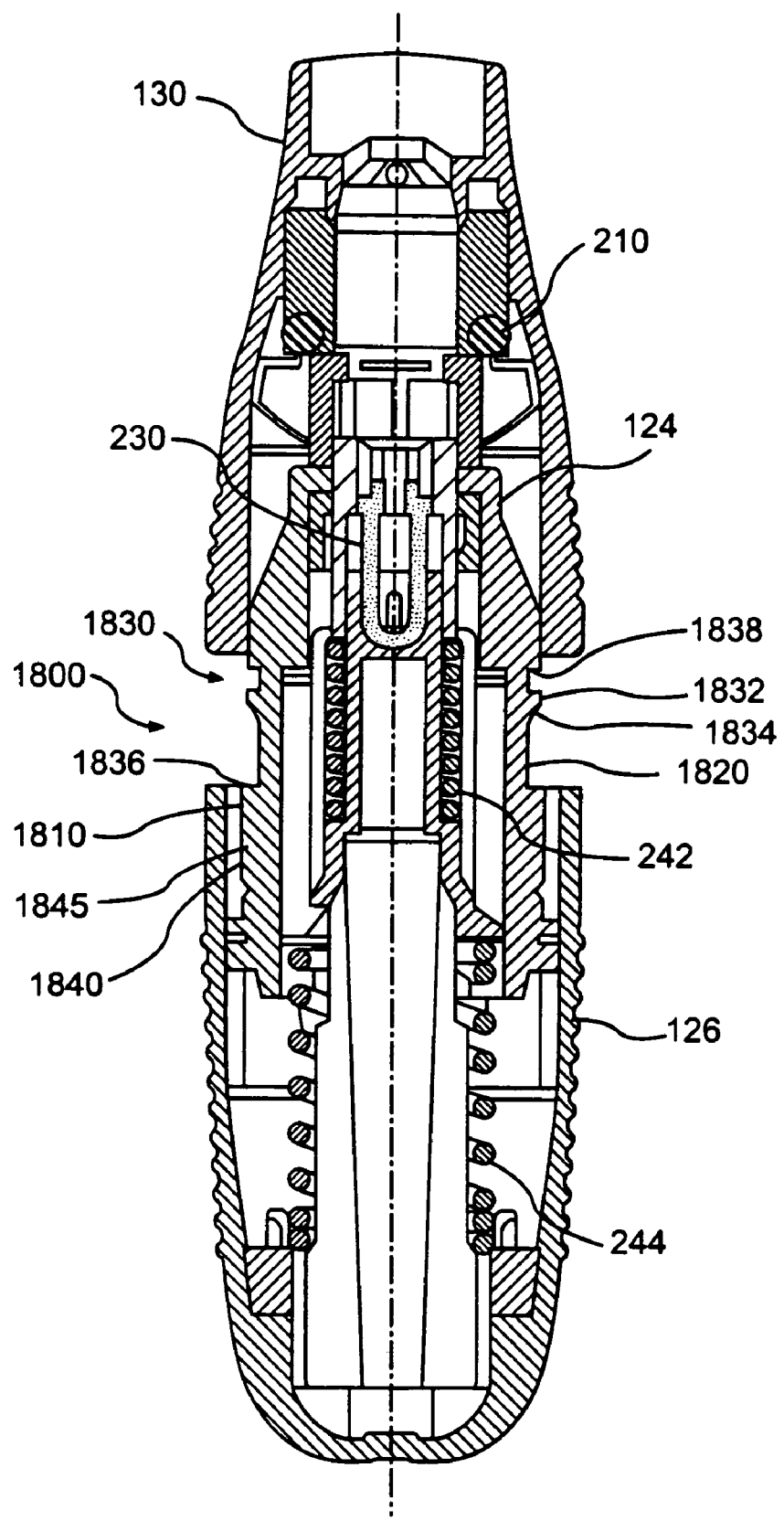
FIG. 18 is a front cross-sectional view of an alternative embodiment of the device for administering powder comprising a means for indicating the readiness of the device.
Figure 19A:
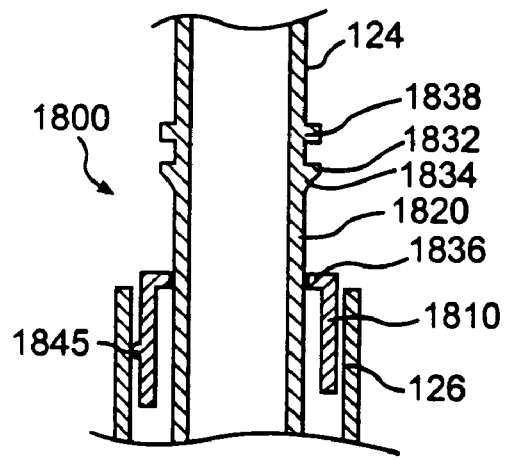
FIGS. 19A-19C are enlarged partial cross-sectional views of a preferred embodiment of the means for indicating readiness of the device.
Figure 19B:
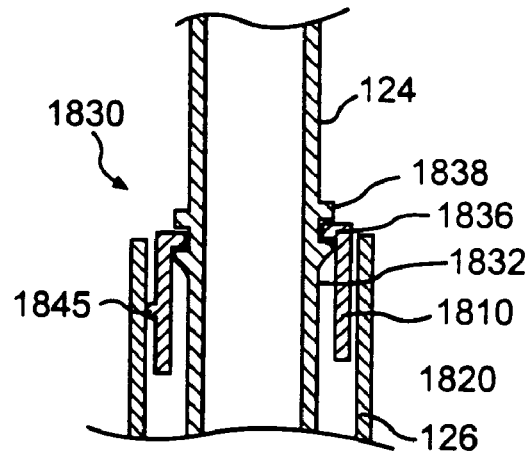
Figure 19C:
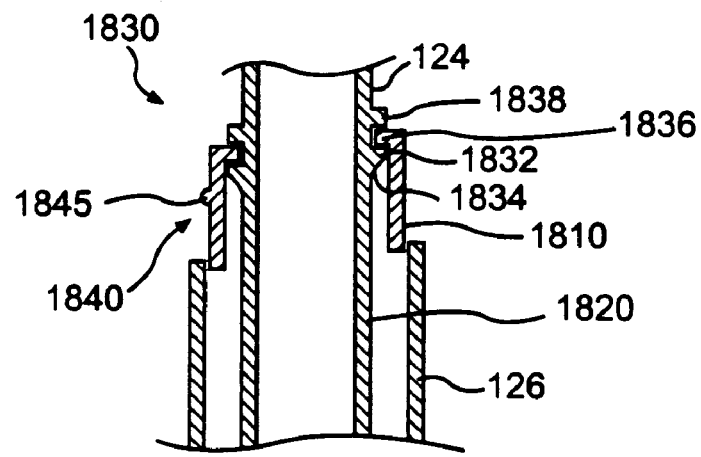

As shown in FIGS. 18 and 19A-19C, in another embodiment of the present invention, device 100 comprises a means for indicating readiness 1800 of the device for emitting powder. The means for indicating readiness 1800 comprises a body 1820 coupled to inner casing 124 and disposed in outer casing 126. Body 1820 is reversibly moveable between a first position, as shown in FIGS. 18, 19A and 19C, and a second position, as shown in FIG. 19B. Body 1820 preferably is coupled to compression spring 244 so that it is biased in the first position. In a preferred embodiment, body 1820 comprises a hollow tube of oblong cross section, although it should be understood that body 1820 may have any other suitable shape, such as a round cylinder or rod.

Means for indicating readiness 1800 further comprises an indicator 1810 disposed in outer casing 126. Indicator 1810 is reversibly moveable between a rest position, as shown in FIGS. 18, 19A and 19B, and an indicating position, as shown in FIG. 19C. Indicator 1810 preferably comprises a hollow ring of oblong cross section, although it should be understood that indicator may have any other suitable shape, such as a round cylinder, a rod, or a plate.

Means for indicating readiness 1800 further comprises a means 1830 for coupling body 1820 and indicator 1810. In a preferred embodiment, coupling means 1830 comprises at least one lip 1836 coupled to indicator 1810 and a corresponding at least one flange 1832 coupled to indicator 1810. Each flange 1832 preferably comprises a ratchet surface 1834 to facilitate coupling and to prevent inadvertent decoupling of each lip 1836 and each flange 1832. In addition, each flange 1832 preferable also comprises a stop 1838 to prevent indicator 1810 from riding up body 1820 beyond each flange 1832. Although a preferred embodiment is illustrated, coupling means 1830 may comprise any other suitable structure for coupling body 1820 and indicator 1810, such as, for example, a friction fit engagement, a plurality of corresponding tangs and grooves, a clip, or a hook and loop fastener.

In a preferred embodiment, as shown in FIG. 19A, before device 100 is actuated, body 1820 is biased in the first position and indicator 1810 is in the rest position and is substantially within outer casing 126, so as to not be visible to the user. When device 100 is actuated to puncture a receptacle, body 1820 moves from the first position to the second position and further into outer casing 126, as shown in FIG. 19B. When in the second position, coupling means 1830 causes body 1820 to become coupled to indicator 1810. In the preferred embodiment illustrated in FIG. 19B, lip 1836 rides over ratchet surface 1834 of flange 1832 and becomes locked between flange 1832 and stop 1838. Preferably, indicator 1810 makes an audible click when it becomes coupled to flange 1832, which informs the user that the device has been actuated properly.

After device 100 is actuated, body 1820 is released and allowed to return to the first position, as shown in FIG. 19C. Because body 1820 is coupled to indicator 1810, the movement of body 1820 to the first position causes indicator 1810 to move from the rest position to the indicating position. In the indicating position, indicator 1810 is at least partially outside of outer casing 126 so that indicator 1810 is visible to the user to indicate that device 100 is ready for inhalation. Indicator 1810 preferably has a bright color, such as, for example, green, to be easily visible.

Upon subsequent actuations of device 100, indicator 1810 remains coupled to body 1820 and moves between the indicating position and the rest position as body 1820 moves between the first position and the second position, respectively, as shown in FIGS. 19B and 19C. In a preferred embodiment, indicator 1810 is equipped with a means 1840 for decoupling indicator 1810 from body 1820, in order to return indicator 1810 to the rest position while body 1820 remains in the first position, as shown in FIG. 19A. The decoupling means 1840 is configured so that applying an axial force to indicator 1810 decouples indicator 1810 from body 1820. In a preferred embodiment illustrated in the figures, decoupling means 1840 comprises at least one knob 1845 coupled to indicator 1810 to facilitate the user returning indicator 1810 to the rest position. It should be understood that decoupling means 1840 may have any other suitable structure, including a plurality of grooves or knobs or another type of easily graspable surface.

In the embodiment shown in FIGS. 19A-19C, indicator 1810 is disposed almost completely within outer casing 126 while in the rest position and is disposed partially within outer casing 126 when in the indicating position. However, it should be understood that a wide variety of other configurations are within the scope of the present invention. For example, indicator 1810 may be disposed substantially within outer casing 126 at both the rest position and the indicating position and may be viewable in one or both of these positions through a window in outer casing 126. In another alternative embodiment, indicator 1810 may be disposed in upper casing portion 130. In yet another alternative embodiment, indicator 1810 may be interchanged with body 1820 such that, for example, the body comprises a ring surrounding the indicator and the indicator is viewable through a window in the body and/or in the outer casing. In yet another alternative embodiment, indicator 1810 may be disposed in the indicating position before device 100 is ready for inhalation and in the rest position when device 100 is ready for inhalation, particularly in an embodiment in which indicator 1810 is viewable through a window in outer casing 126.

Means for indicating 1800 may be used with any type of inhaler, or any another type of device that utilizes a body to which is applied an axial force. For example, in an alternative embodiment, means for indicating 1800 may be used to indicate that an epinephrine injection pen, used for treating allergies, has been used or is ready for use. In another alternative embodiment, means for indicating 1800 may be used to indicate that an aerosol canister inhaler has been used or is ready for use. Means for indicating 1800 may be used with both single-use and multiple-use devices. In addition, a device containing a plurality of inhalation chambers and a plurality of receptacles may comprise a plurality means for indicating 1800.

CONCLUSION

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

What is claimed is:

1. A device for emitting powder, comprising:
   a casing, said casing comprising at least one aperture configured to emit powder therethrough;
   a cylindrical chamber, defined by a straight wall of circular cross-section, disposed in said casing, said chamber having a proximal end and a distal end, said chamber comprising a ring circumferentially coupled to an inner surface of said chamber;
   a powder capsule disposed in said chamber;
   a substantially longitudinal prong, comprising a distal end, a proximal end, and a periphery, disposed in said casing;
   a sharp puncturing point, disposed on the distal end of the prong, wherein the sharp puncturing point makes the initial puncture in the powder capsule;

a primary cutting edge disposed on the periphery of the prong, running from the proximal end of the prong to the distal end of the prong, and terminating at the sharp puncturing point; and a substantially planar face disposed on the periphery of the prong opposite of the primary cutting edge, a distal end of the substantially planar face terminating at an edge opposite the sharp puncturing point; and wherein the substantially longitudinal prong creates an opening in said powder capsule by forming a hanging chad in said powder capsule, the hanging chad having a free end formed by the sharp puncturing point and the primary cutting edge. and a hinge coupled to said powder capsule formed by the substantially planar face and the edge.

2. A device for emitting powder, comprising:

a casing, said casing comprising at least one aperture configured to emit powder therethrough;

a cylindrical chamber, defined by a straight wall of circular cross-section, disposed in said casing, said chamber having a proximal end and a distal end, said chamber comprising a ring circumferentially coupled to an inner surface of said chamber;

a powder capsule disposed in said chamber;

a substantially longitudinal prong, comprising a distal end, a proximal end, and a periphery, disposed in said casing;

a sharp puncturing point, disposed on the distal end of the prong, wherein the sharp puncturing point makes the initial puncture in the powder capsule;

a primary cutting edge disposed on the periphery of the prong, running from the proximal end of the prong to the distal end of the prong, and terminating at the sharp puncturing point;

a substantially planar face disposed on the periphery of the prong opposite of the primary cutting edge, a distal end of the substantially planar face terminating at an edge opposite the sharp puncturing point; and wherein the substantially planar face and the edge form a hanging chad in a wall of the powder capsule, wherein the powder capsule has a longitudinal axis substantially parallel to the prong and a minor axis substantially perpendicular to the longitudinal axis, the hanging chad being opened to an angle of at least 30 degrees with respect to the minor axis.

3. The device of claim 2, wherein the hanging chad is opened to an angle between 30 and 45 degrees with respect to the minor axis.

4. A device for emitting powder, comprising:

a casing, said casing comprising at least one aperture configured to emit powder therethrough;

a powder capsule disposed in said casing;

a puncturing device, disposed in said casing, for puncturing said powder capsule, wherein said puncturing device comprises, a substantially longitudinal prong comprising a distal end, a proximal end, and a periphery, a sharp puncturing point, disposed on the distal end of the prong, wherein the sharp puncturing point makes the initial puncture in said powder capsule, a primary cutting edge disposed on the periphery of the prong and terminating at the sharp puncturing point, a face disposed on the periphery of the prong opposite of the primary cutting edge, a distal end of the face terminating at an edge opposite the sharp puncturing point, and wherein the prong creates an opening in said powder capsule by forming a hanging chad in said powder capsule, the hanging chad having a free end formed by the sharp puncturing point and the primary cutting edge, and a hinge coupled to said powder capsule formed by the face and the edge.

5. The device of claim 4, wherein the prong further comprises a base coupled to the proximal end of the prong.

6. The device of claim 4, wherein the primary cutting edge is sharp.

7. The device of claim 4, wherein the primary cutting edge is jagged.

8. The device of claim 4, wherein the primary cutting edge is serrated.

9. The device of claim 4, wherein the face has a concave curvature.

10. The device of claim 4, wherein the prong is tapered so that the distal end of the prong is smaller than the proximal end of the prong, to facilitate removing the prong from the powder capsule.

11. The device of claim 4, further comprising an angled surface disposed on the distal end of the prong, the angled surface having a distal end terminating at the sharp puncturing point and a proximal end terminating at the edge.

12. The device of claim 4, wherein the puncturing device is made of metal.

13. The device of claim 4, wherein the puncturing device is made of ceramic.

14. The device of claim 4, wherein the puncturing device is made of plastic.

15. The device of claim 4, further comprising:

a plurality of longitudinal faces and a plurality of longitudinal edges disposed on the periphery of the prong between the primary cutting edge and the face, and running from the proximal end of the prong to the distal end of the prong.

16. The device of claim 15, wherein the number of longitudinal faces is four.

17. The device of claim 15, wherein the number of longitudinal faces is two.

18. The device of claim 15, wherein the number of longitudinal edges is four.

19. The device of claim 15, wherein the number of longitudinal edges is two.

20. The device of claim 15, wherein a cross section of the prong is substantially a pentagon.

21. The device of claim 15, wherein a cross section of the prong is substantially a triangle.

22. The device of claim 15, wherein one or more of the plurality of longitudinal edges is sharp.

23. The device of claim 15, wherein one or more of the plurality of longitudinal edges is jagged.

24. The device of claim 15, wherein one or more of the plurality of longitudinal edges is serrated.

25. The device of claim 15, wherein one or more of the plurality of longitudinal edges is blunt.

26. The device of claim 15, wherein each of the plurality of longitudinal faces is substantially planar.

27. The device of claim 15, wherein each of the plurality of longitudinal faces has a concave curvature.

28. The device of claim 4, wherein said puncturing device comprises:

a base; and another substantially longitudinal prong, wherein said substantially longitudinal prong and said another substantially longitudinal prong are coupled to said base to form a U-shape.

29. A device for emitting powder, comprising:
a casing, said casing comprising at least one aperture configured to emit powder therethrough;
a powder capsule disposed in said casing;
a puncturing device, disposed in said casing, for puncturing said powder capsule, wherein said puncturing device comprises,
  a substantially longitudinal prong comprising a distal end, a proximal end, and a periphery,
  a sharp puncturing point, disposed on the distal end of the prong, wherein the sharp puncturing point makes the initial puncture in the powder capsule,
  a primary cutting edge disposed on the periphery of the prong and terminating at the sharp puncturing point,
  a face disposed on the periphery of the prong opposite of the primary cutting edge, a distal end of the face terminating at an edge opposite the sharp puncturing point, and
  wherein the face and the edge form a hanging chad in a wall of said powder capsule, wherein said powder capsule has a longitudinal axis substantially parallel to the prong and a minor axis substantially perpendicular to the longitudinal axis, the hanging chad being opened to an angle of at least 30 degrees with respect to the minor axis.

30. The device of claim 29, wherein the prong further comprises a base coupled to the proximal end of the prong.

31. The device of claim 29, wherein the primary cutting edge is sharp.

32. The device of claim 29, wherein the primary cutting edge is jagged.

33. The device of claim 29, wherein the primary cutting edge is serrated.

34. The device of claim 29, wherein the face has a concave curvature.

35. The device of claim 29, wherein the prong is tapered so that the distal end of the prong is smaller than the proximal end of the prong, to facilitate removing the prong from the powder capsule.

36. The device of claim 29, further comprising an angled surface disposed on the distal end of the prong, the angled surface having a distal end terminating at the sharp puncturing point and a proximal end terminating at the edge.

37. The device of claim 29, wherein the puncturing device is made of metal.

38. The device of claim 29, wherein the puncturing device is made of ceramic.

39. The device of claim 29, wherein the puncturing device is made of plastic.

40. The device of claim 29, further comprising:
a plurality of longitudinal faces and a plurality of longitudinal edges disposed on the periphery of the prong between the primary cutting edge and the face, and running from the proximal end of the prong to the distal end of the prong.

41. The device of claim 40, wherein the number of longitudinal faces is four.

42. The device of claim 40, wherein the number of longitudinal faces is two.

43. The device of claim 40, wherein the number of longitudinal edges is four.

44. The device of claim 40, wherein the number of longitudinal edges is two.

45. The device of claim 40, wherein a cross section of the prong is substantially a pentagon.

46. The device of claim 40, wherein a cross section of the prong is substantially a triangle.

47. The device of claim 40, wherein one or more of the plurality of longitudinal edges is sharp.

48. The device of claim 40, wherein one or more of the plurality of longitudinal edges is jagged.

49. The device of claim 40, wherein one or more of the plurality of longitudinal edges is serrated.

50. The device of claim 40, wherein one or more of the plurality of longitudinal edges is blunt.

51. The device of claim 40, wherein each of the plurality of longitudinal faces is substantially planar.

52. The device of claim 40, wherein each of the plurality of longitudinal faces has a concave curvature.

53. The device of claim 29, wherein said puncturing device comprises:
a base; and
another substantially longitudinal prong, wherein said substantially longitudinal prong and said another substantially longitudinal prong are coupled to said base to form a U-shape.

* * * * *